US010368852B2

(12) United States Patent
Gerhardt et al.

(10) Patent No.: US 10,368,852 B2
(45) Date of Patent: Aug. 6, 2019

(54) ORIENTATION DEVICE FOR USE IN MITRAL VALVE REPAIR

(71) Applicant: STRAIT ACCESS TECHNOLOGIES HOLDINGS (PTY) LTD, Cape Town (ZA)

(72) Inventors: Thomas Gerhardt, Cape Town (ZA); Michael Alan Cousins, Cape Town (ZA); Peter Rudi Haw, Cape Town (ZA); Jeremy Douglas Jarman, Cape Town (ZA); Edward Charles Mudge, Cape Town (ZA); Heather Madeleine Coombes, Cape Town (ZA); Deon Bezuidenhout, Cape Town (ZA); Peter Paul Zilla, Cape Town (ZA)

(73) Assignee: STRAIT ACCESS TECHNOLOGIES HOLDINGS (PTY) LTD, Cape Town (ZA)

( * ) Notice: Subject to any disclaimer, the term of this patent is extended or adjusted under 35 U.S.C. 154(b) by 532 days.

(21) Appl. No.: 14/392,125

(22) PCT Filed: Jun. 26, 2014

(86) PCT No.: PCT/IB2014/062630
§ 371 (c)(1),
(2) Date: Dec. 23, 2015

(87) PCT Pub. No.: WO2014/207699
PCT Pub. Date: Dec. 31, 2014

(65) Prior Publication Data
US 2016/0183931 A1 Jun. 30, 2016

(30) Foreign Application Priority Data
Jun. 26, 2013 (ZA) .................................. 2013/04771

(51) Int. Cl.
A61M 25/04 (2006.01)
A61B 5/0215 (2006.01)
(Continued)

(52) U.S. Cl.
CPC .... A61B 17/00234 (2013.01); A61B 5/02158 (2013.01); A61B 17/3468 (2013.01);
(Continued)

(58) Field of Classification Search
CPC ...... A61B 17/3468; A61B 2017/00022; A61B 2017/00238; A61B 2017/00243;
(Continued)

(56) References Cited

U.S. PATENT DOCUMENTS 7,635,329 B2 * 12/2009 Goldfarb ............ A61B 17/0401
600/37
7,803,168 B2 9/2010 Gifford et al.
(Continued)

OTHER PUBLICATIONS

International Search Report issued in PCT/IB2014/062630 dated Oct. 16, 2014 (2 pages).
(Continued)

Primary Examiner — Ryan J. Severson
(74) Attorney, Agent, or Firm — Osha Liang LLP

(57) ABSTRACT

An orientation device (200) for use in mitral valve repair surgery is provided and includes a catheter (202) catheter insertable percutaneously through the mitral valve into a chamber of a heart. At least one pressure sensor (216, 218) and two generally arcuate commissural arms (208, 210) are provided at or near the distal end (204) of the catheter (202). The arms (208, 210) are deployable from a stowed condition, in which the catheter (202) can be introduced percutaneously into the heart, to an operative condition in which they extend outwardly in generally opposite directions. Each arm (208, 210) is shaped to be locatable within a mitral valve
(Continued)

commissure and has an indentation (212) shaped to extend, in use, at least partially about a mitral valve commissure to limit movement of the device (200) relative to the mitral valve in the axial direction of the catheter (202).

14 Claims, 18 Drawing Sheets

(51) Int. Cl.
*A61B 17/00* (2006.01)
*A61B 17/34* (2006.01)
*A61M 25/00* (2006.01)
*A61B 17/22* (2006.01)
*A61B 90/00* (2016.01)

(52) U.S. Cl.
CPC ... *A61M 25/04* (2013.01); *A61B 2017/00022* (2013.01); *A61B 2017/00243* (2013.01); *A61B 2017/00327* (2013.01); *A61B 2017/00557* (2013.01); *A61B 2017/00867* (2013.01); *A61B 2017/22068* (2013.01); *A61B 2017/22098* (2013.01); *A61B 2017/3425* (2013.01); *A61B 2017/3488* (2013.01); *A61B 2090/064* (2016.02); *A61M 25/0074* (2013.01); *A61M 2025/0002* (2013.01)

(58) Field of Classification Search
CPC .......... A61B 2017/00292; A61B 2017/00327; A61B 2017/00557; A61B 2017/00783; A61B 2017/22068; A61B 2017/22069; A61B 2017/22098; A61B 2017/3484; A61B 2017/3488; A61B 5/021; A61B 5/02141; A61B 5/0215; A61B 5/02158; A61M 2025/0002; A61M 25/0074; A61M 25/04
See application file for complete search history.

(56) References Cited

U.S. PATENT DOCUMENTS

| | | | |
|---|---|---|---|
| 7,998,151 B2* | 8/2011 | St. Goar | A61B 17/0469 606/139 |
| 8,974,475 B2* | 3/2015 | Rothstein | A61B 17/0401 606/142 |
| 9,554,816 B2* | 1/2017 | Golan | A61B 17/22 |
| 2005/0021057 A1 | 1/2005 | St. Goar et al. | |
| 2006/0116590 A1* | 6/2006 | Fayram | A61B 5/0215 600/508 |
| 2007/0197858 A1 | 8/2007 | Goldfarb et al. | |
| 2008/0021552 A1 | 1/2008 | Gabbay | |
| 2011/0270276 A1 | 11/2011 | Rothstein et al. | |
| 2012/0209375 A1 | 8/2012 | Madrid et al. | |
| 2012/0253358 A1 | 10/2012 | Golan | |
| 2016/0183931 A1* | 6/2016 | Gerhardt | A61B 17/00234 606/130 |

OTHER PUBLICATIONS

Written Opinion of the International Searching Authority issued in PCT/IB2014/062630 dated Oct. 16, 2014 (7 pages).

* cited by examiner

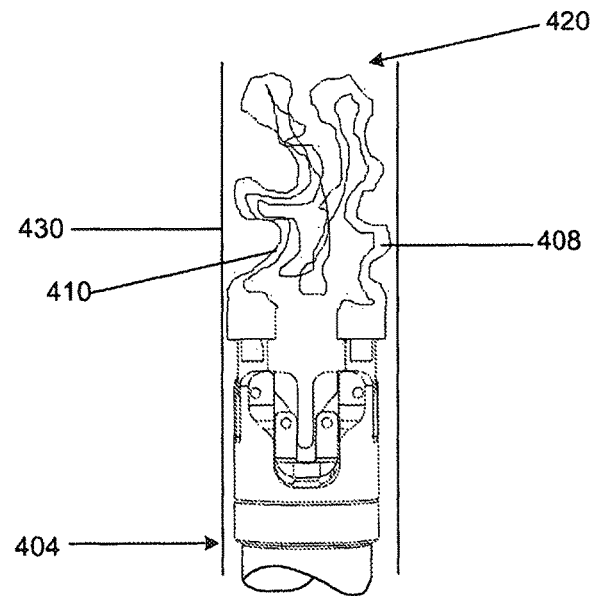
Figure 11
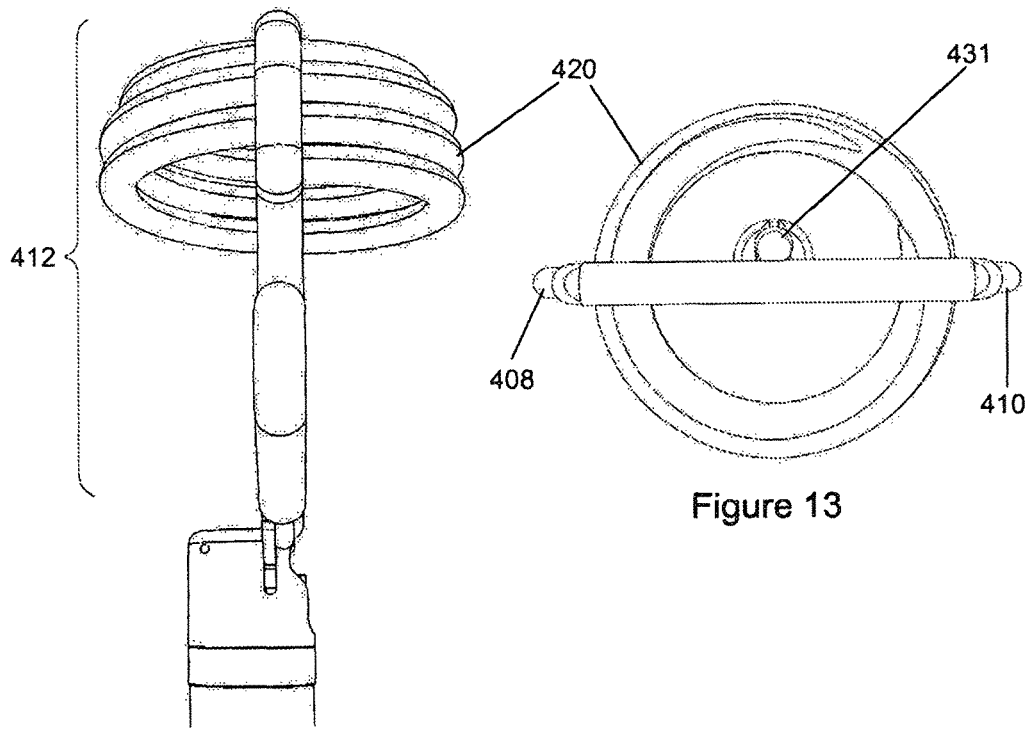
Figure 12
Figure 13

ORIENTATION DEVICE FOR USE IN MITRAL VALVE REPAIR

CROSS-REFERENCE(S) TO RELATED APPLICATIONS

This application claims priority from South African provisional patent application number 2013/04771, which is incorporated by reference herein.

FIELD OF THE INVENTION

This invention relates to devices for use during percutaneous mitral valve repair procedures.

BACKGROUND TO THE INVENTION

The mitral valve in the heart of vertebrate animals is a bicuspid one-way valve situated on the left side of the heart and isolates the left atrium from the left ventricle. It comprises two leaflets of flexible collagenous material which, in normal operation, open as the left ventricle relaxes and dilates (diastole), thereby permitting oxygenated blood from the lungs to flow from the left atrium into the left ventricle. The mitral valve coapts (closes) during the contraction cycle (systole) of the left ventricle to prevent the blood from returning to the left atrium. The blood is then forced to exit the left ventricle through the aortic valve and flows to the rest of the body.

A mitral annulus, which is a fibrous ring having a malformed "D" shape supports the leaflets around their peripheries. The annulus lies in a plane generally perpendicular to the average blood flow direction through the valve. Chordae tendineae are string-like structures which extend between and link papillary muscles found on the lower portion of the interior wall of the left ventricle and the free edges of the mitral valve leaflets. These structures prevent the valve from prolapsing into the left atrium during systole.

Mitral valve regurgitation (MR) is a common heart condition caused by improper closing of the valve due to deterioration of the mitral valve and/or surrounding anatomy. MR involves the backflow of blood from the left ventricle into the left atrium during contraction of the left ventricle. As a result, the left ventricle has to pump progressively harder to circulate the blood throughout the body, thereby increasing the risk of congestive heart failure.

Currently a number of percutaneous mitral valve therapies are available to repair or replace dysfunctional mitral valves. Examples of these procedures are annuloplasty, leaflet resection, valvulotomy, valvuloplasty and leaflet plication. A common approach used to access the mitral valve for surgical procedures is through the apex of the heart via a transapical port. An incision is made in the chest wall of a patient and a catheter is advanced through the apex of the heart towards the mitral valve.

Accessing the mitral valve in this way is generally performed using radiopaque markers and fluoroscopy or other imaging systems such as intravascular sound imaging, transoesophageal echocardiography and angiography. Transapical access is further complicated by the presence of the sub-valvular apparatus, which includes the chordae tendineae, the papillary muscles as well as parts of the ventricular wall, which can entangle and hinder access to the mitral valve.

As it is essential to be properly positioned and orientated within the mitral valve annulus to perform surgical techniques, these techniques require specialised and expensive imaging equipment. This typically limits their application in developing and third world countries where such equipment is not readily available.

There is thus a need for cost effective and accurate methods and devices for gaining access to heart valves which do not require complex imaging techniques and equipment to perform replacement or repair surgery.

SUMMARY OF THE INVENTION

In accordance with the invention there is provided an orientation device for use in mitral valve repair surgery, the device including a catheter insertable percutaneously through the mitral valve into a chamber of a heart, the catheter having a distal end configured for entering the heart and a proximal end for manipulating the device, characterised in that the device includes at least one pressure sensor at or near the distal end of the catheter and two generally arcuate commissural arms at or near the distal end of the catheter, the arms being deployable from a stowed condition, in which the catheter can be introduced percutaneously into the heart, to an operative condition in which the arms extend outwardly in generally opposite directions, each arm being shaped to be locatable within a mitral valve commissure to limit rotational movement of the catheter relative to the mitral valve without affecting the function of the valve.

A further feature provides for each commissural arm to have an indentation shaped to extend, in use, at least partially about a mitral valve commissure, at the level of the valve annulus, to limit movement thereof relative to the mitral valve in the axial direction of the catheter.

In one embodiment of the invention, the commissural arms include a pair of elongate flexible members that are individually operable and partially rotatable about the catheter. In this embodiment, the elongate members are flexible wires which may be deployed to an operatively arcuate condition by means of a pull and/or push wire arrangement; alternatively for the wires to be manufactured from a shape memory alloy and each of which is pre-formed and held in a deformed, relatively unbent shape during entry of the device into the heart, and returns to their pre-formed bent shape through manipulation of the device from its stowed condition to its operative condition.

In an alternative embodiment of the invention, the commissural arms are tubular and capable of receiving a fluid therein. Further features of this embodiment provide for at least part of each arm to include an inflatable member; for the arms to be pivotable relative to the catheter; and for the arms to form a continuous loop.

Still further features of this embodiment provide for the device to include a probe which extends from the catheter and which is movable relative to the commissural arms and extends, in use, through a mitral valve; for the probe to be movable by means of a pull and/or push wire arrangement; for the probe to be capable of bending along its length by means of a pull and/or push wire arrangement; and for the probe to be rotatable.

Further features of the invention provide for an atrial anchor to be associated with the distal end of the catheter and which can be deployed from an inoperative condition, in which it can be introduced percutaneously into the heart and into the left atrium, to an operative condition, in which it forms an annular shape which is locatable in or over the mitral valve annulus and is too large to pass therethrough so as to provide a reference axis for axial and angular orientation; for the atrial anchor to be integral with the tubular members, alternatively to at least partially include a tubular member capable of receiving a fluid therein; for the anchor to be formed by a looped element; and for the looped element to assume any suitable shape, preferably a helical shape when in the operative condition.

Further features of the invention provide for the device to include two pressure sensors spaced apart along the length of the catheter; for a first pressure sensor to be located at or near the distal end of the catheter and for a second pressure sensor to be spaced apart therefrom such that, in use, the first pressure sensor is capable of measuring pressure within a heart chamber on one side of the mitral valve and the second sensor is capable of measuring pressure in the heart chamber on the opposite side of the mitral valve.

Further features of the invention provide for a location device to be associated with the distal end of the catheter for navigating the distal end of the catheter from the left ventricle through the mitral valve and into the left atrium; for location device to be capable of being manipulated from a stowed condition, in which it can be introduced percutaneously into the heart, to an operative condition in which it assumes a shape which enables the device to be navigated through the mitral valve without entanglement in the sub-valvular apparatus; for the location device to have an at least partially domed structure, which, in the operative condition, is capable of deflecting the sub-valvular apparatus in the left ventricle away from the catheter to permit the catheter to be directed into the mitral valve; for the domed structure to include a surface shaped to bear on a wall of the left ventricle to so direct the device through the chordae into the mitral valve; for the domed structure to be provided by elongate members; and for the elongate members to be flexible; alternatively for the elongate members to be tubular and capable of being inflated with a fluid.

The invention further provides a manipulation device for use in mitral valve repair surgery, the device including a catheter insertable percutaneously through the mitral valve, the catheter having a distal end configured for entering the heart and a proximal end for manipulating the device, characterised in that the device includes at least one pressure sensor at or near the distal end of the catheter and is capable of being secured to an anchor assembly located in a mitral valve and wherein a movable probe is provided on the catheter which can be moved within the zone of coaptation of the mitral valve and which can be used to manipulate the valve.

Further features of the invention provide for the anchor assembly to include two generally arcuate commissural arms which extend outwardly in generally opposite directions and are shaped to be locatable within a mitral valve commissure and have an indentation shaped to extend, in use, at least partially about a mitral valve commissure; and for the anchor assembly to further include an atrial anchor which operatively forms an annular shape which is locatable in or over the mitral valve annulus and is too large to be withdrawn therethrough.

Still further features of the invention provide for the probe to be capable of bending along its length; and for the probe to be operatively rotatable within a mitral valve.

The invention further provides a method of positioning a catheter relative to a mitral valve, the method comprising the steps of:
    extending the distal end of a catheter having at least one pressure node at or near its distal end though the mitral valve from either the left ventricle into the left atrium of a heart or from the left atrium into the left ventricle of a heart,
    taking an initial pressure measurement in the ventricle and an initial pressure measurement in the atrium using the at least one pressure node,
    extending within the mitral valve a pair of arms from the distal end of the catheter which arms project outwardly in generally opposite directions and are shaped to be locatable within a mitral valve commissure and have an indentation shaped to extend at least partially about a mitral valve commissure,
    measuring pressure in one or both of the left ventricle and left atrium and comparing the measurement to the initial pressure measurement in the corresponding chamber,
    rotating the arms within the mitral valve if the measurement is not substantially similar to the corresponding initial pressure measurement,
    repeating the steps of measuring pressure in one or both of the left ventricle and left atrium, comparing the measurement to the corresponding initial pressure measurement and rotating the arms within the mitral valve if the measurement is not substantially similar to the corresponding initial pressure measurement until the measurement is substantially similar to the corresponding initial pressure measurement, and
    moving the arms axially within the valve until the indentation in each arm extends about a mitral valve commissure.

Further features of the invention provide for an atrial anchor having an annular shape to be deployed in the left atrium in or over the mitral annulus; and for a probe or rod-like member to be moved within the zone of coaptation of the mitral valve; and for pressure measurements to be made during such movement.

BRIEF DESCRIPTION OF THE DRAWINGS

The invention will now be described, by way of example only with reference to the accompanying representations in which:

FIGS. 3A and 3B are anterior views of a second embodiment of a location device in which FIG. 3A illustrates the location device in a partially operative condition and FIG. 3B illustrates the location device in a fully operative condition;

FIG. 11 is part sectional anterior view of part of the orientation device in FIG. 9 with the commissural arms in a stowed condition;

FIG. 12 is a medio-lateral view of part the orientation device in FIG. 9;

FIG. 13 is an atrial view of the orientation device in FIG. 9;

DETAILED DESCRIPTION WITH REFERENCE TO THE DRAWINGS

Percutaneous mitral valve repair or replacement involves highly complex surgical procedures. One reason for this complexity is that the surgery is carried out on an active heart, requiring the surgeon to enter the heart, locate the mitral valve and then perform the procedure while the valve is opening and closing. It is therefore of utmost importance that the surgeon is able to accurately and effectively locate and orientate any surgical equipment with relation to the mitral valve. Furthermore, while locating and repairing the mitral valve, it is important that the effect of the procedure on the normal operation of the heart is kept to a minimum so as to prevent the patient from going into cardiac arrest or the like. Thus, blood flow must not be disrupted to any significant degree.

Figure 1:
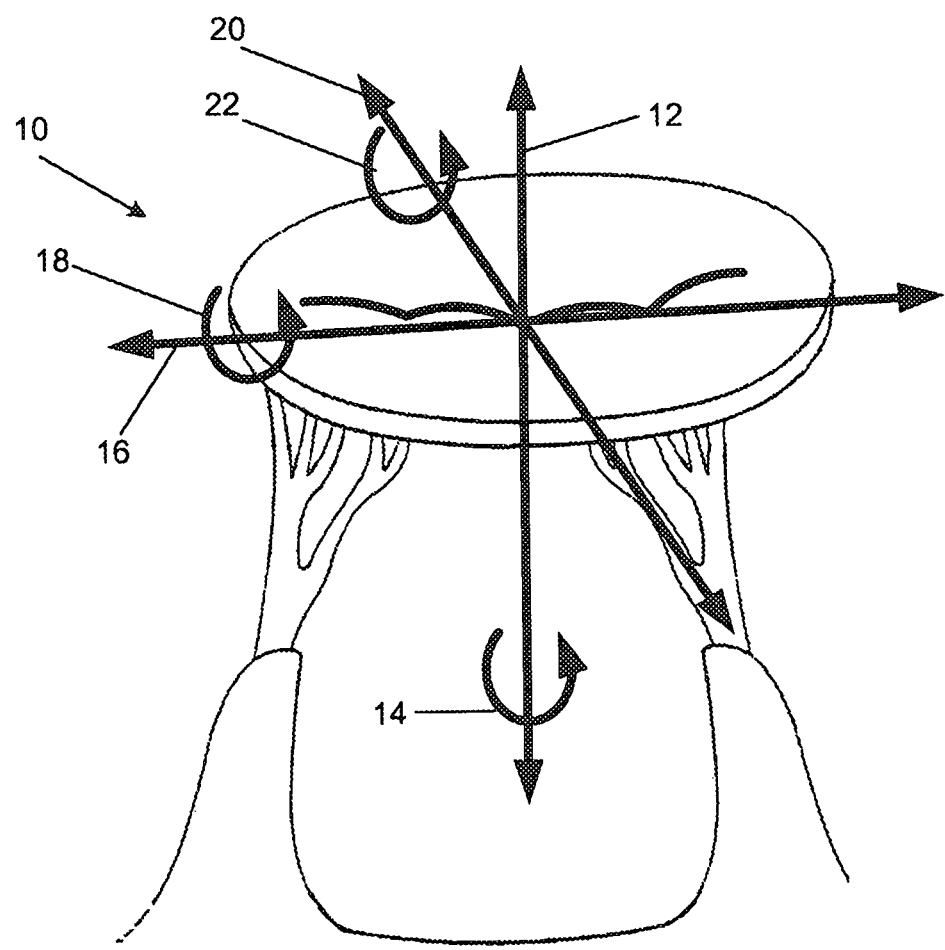
FIG. 1 is a schematic drawing illustrating the degrees of freedom considered when assessing the orientation of a mitral valve.

The directional arrows in FIG. 1 illustrate various orientation constraints that are required when positioning a device relative to the mitral valve (10). In order to ascertain the orientation of the mitral valve as well as position a surgical instrument relative to the mitral valve, six degrees of freedom have to be accounted for to ensure accurate orientation within the mitral valve. The orientation considerations necessary are axial (12), rotational about the axial axis (14), mediolateral (16), rotational about the mediolateral axis (18), antero-posterior (20) as well as rotational about the antero-posterior axis (22).

The embodiments described below are intended for use in percutaneous surgery on the mitral valve of the heart. Such procedures typically entail access to the mitral valve either transapically, transfemorally or transaortically. For simplicity, the embodiments described below relate to devices for use in transapical procedures. Unless specifically indicated otherwise, or the contrary is apparent, the devices could equally be adapted for use transfemorally or transaortically. It will be appreciated by those skilled in the art that the direction of approach taken during the percutaneous procedure, that is whether the mitral valve is approached from the left ventricle or the left atrium, will affect the orientation of the operative elements of the device, but not the manner in which they are used or function. Also, whereas devices intended for transapical use can make use of a rigid catheter, those intended for transfemoral and transaortic use will typically employ a steerable catheter. Such catheters are well known in the art.

Transapically accessing the left atrium through the mitral valve requires that the surgeon is enabled to navigate through the left ventricle and the mitral valve into the left atrium without entanglement in the sub-valvular apparatus. This may be difficult where the surgeon does not have optical imaging equipment at his disposal.

Figure 2A:
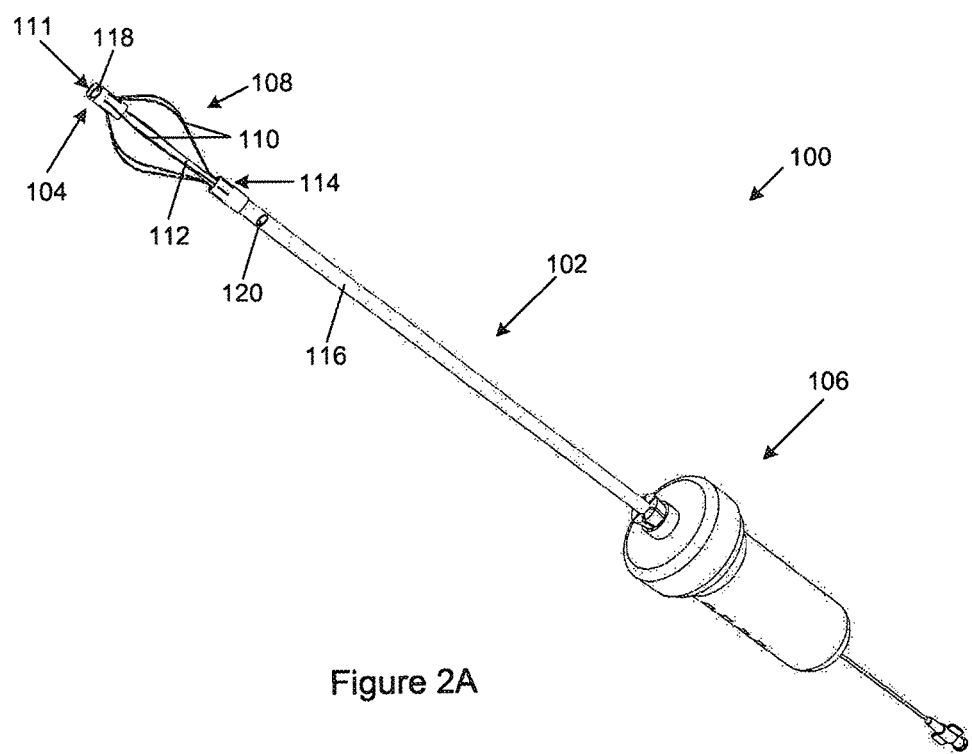
FIGS. 2A and 2B are three-dimensional views of a first embodiment of a location device in which the location device is in an operative condition.
Figure 2B:
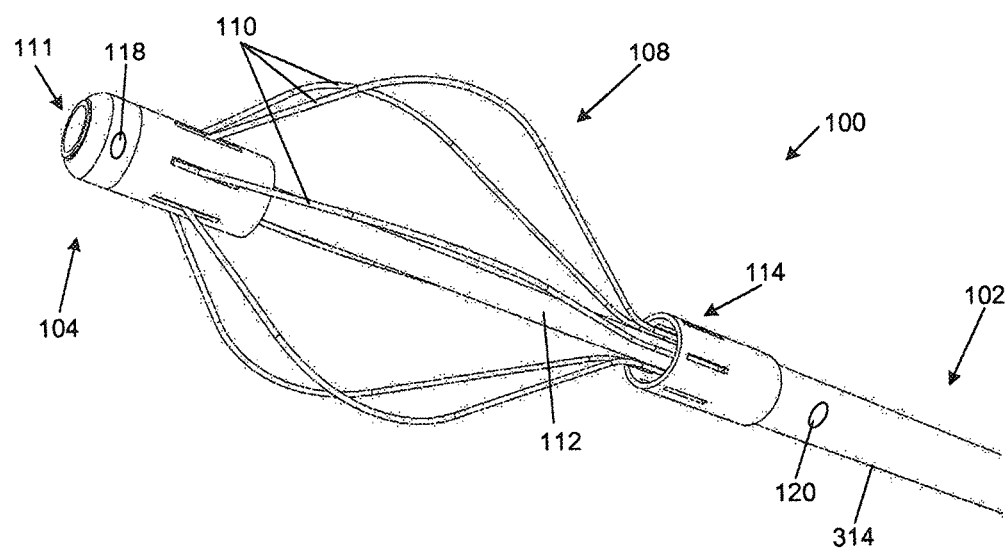

FIGS. 2A and 2B illustrate one embodiment of a location device (100) for transapically accessing and navigating through the left ventricle, and through the mitral valve into the left atrium. The location device (100) includes a catheter (102) which has a distal end (104) which is configured to enter the heart through a transapical port and a proximal end (106) for manipulating the device (100) from a stowed condition, in which it is capable of passing through the transapical port, to an operative condition in which it assumes a shape which enables it to be navigated through the mitral valve without entanglement in the left ventricular space and sub-valvular apparatus.

In order to achieve this, the catheter (102) has a domed structure (108) near its distal end (104). This is formed by a plurality of flexible elongate members (110) which are circumferentially spaced apart and extend in the length of the catheter (102). Each member (110) is attached at one end to the distal end (111) of a first inner sheath (112) and at the opposite end to the distal end (114) of a second outer sheath (116). The inner sheath (112) is slideable within the outer sheath (116) and extends beyond the distal end (114) of the outer sheath (116). When the distal end (111) of the inner sheath (112) is drawn towards the distal end (114) of the outer sheath (116), the members (110) flex radially outwardly to form the domed structure (108). The domed structure (108) acts to operatively deflect the left ventricular and sub-valvular apparatus away from the catheter so as to permit the distal end (104) of the catheter (102) to be directed into the mitral valve without entanglement in the anatomical structures.

Furthermore, in order to assist in successfully navigating through the mitral valve, the elongate members (110) forming the domed structure (108) each provide a surface which can bear on a wall of the left ventricle and hold the catheter (102) a distance from the wall such that advancing the catheter (102) towards the mitral valve causes its distal end (104) to be directed into the mitral valve. The shape of the elongate members (110), and thus the domed structure (108), is such that the distal end (104) of the catheter (102) is directed into the mitral valve by bearing the structure (108) on a wall of the left ventricle. At the same time, the structure (108) operatively deflects the left ventricular and sub-valvular apparatus away from the catheter (102) so as to prevent entanglement of the catheter (102) therein.

In order to assist in navigating through the mitral valve, the location device (100) further includes two pressure nodes or sensors (118, 120) which are capable of measuring pressures within the heart. A first pressure sensor (118) is located at the distal end (104) of the catheter (102) and a second pressure sensor (120) is spaced apart therefrom, preferably the axial length of a typical mitral valve. A display (not shown) at the proximal end of the catheter (102)

shows the pressure measured by each sensor (118, 120). Systolic pressure within the left atrium ranges from 15 to 30 mmHg whereas systolic pressure within the left ventricle ranges from 100 to 140 mmHg. When both sensors (118, 120) are in the ventricle they will both indicate the same pressure, normally one in the range 100 to 140 mmHg. These pressures may vary considerably in a pathological situation where a diseased mitral valve is encountered. Nevertheless there will usually be a significant pressure difference between the two chambers, typically greater than 40 mmHg. As the distal end (104) of the catheter (102) is inserted into the mitral valve, the pressure reading of the first pressure sensor (118) will be lower when compared to the reading of the second pressure sensor (120), indicating that the distal end (104) of the catheter (102) has successfully been navigated into the left atrium. Thus the first sensor (118) will indicate a pressure of about 15 to 30 mmHg whereas the second sensor (120) will indicate a pressure of about 100 to 140 mmHg. By monitoring only the readings on the pressure sensors the surgeon is thus able to determine with a high degree of certainty whether the catheter (102) has successfully been navigated through the mitral valve and into the left atrium.

Figures 3A, 3B:
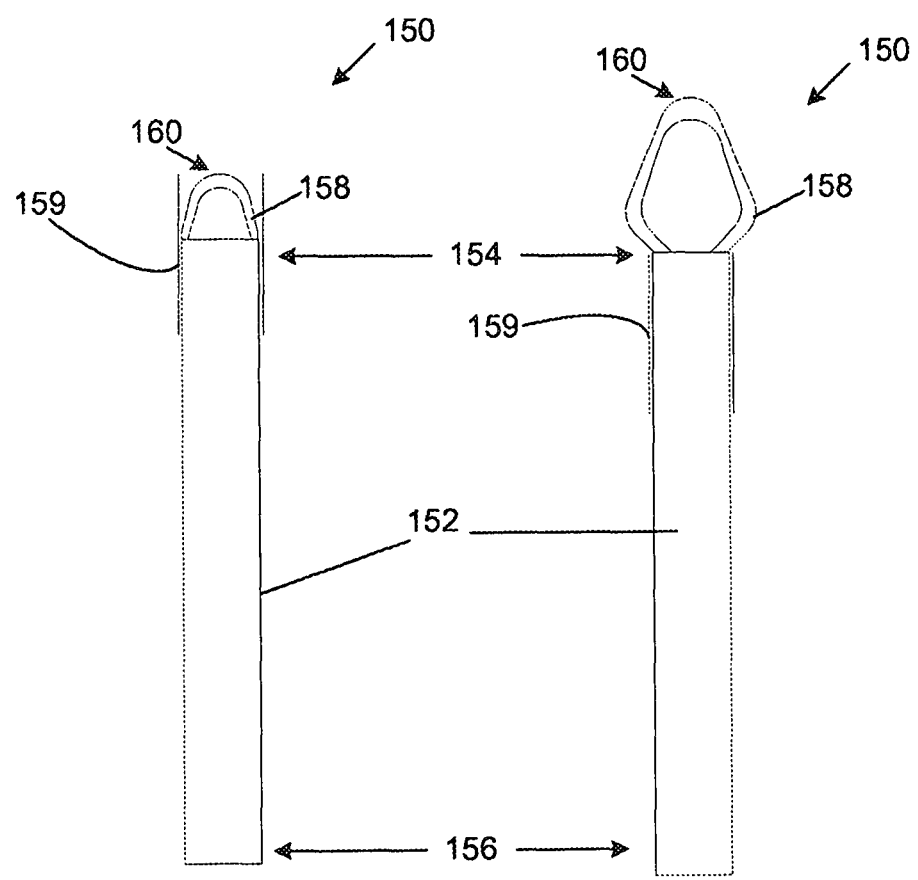

FIGS. 3A and 3B illustrate an alternative embodiment of a location device (150) for transapically accessing and navigating through the left ventricle, and through the mitral valve into the left atrium. The device (150) also includes a catheter (152) which has a distal end (154) which is configured to enter the heart through a transapical port and a proximal end (156) for manipulating the device (150) from a stowed condition, in which it is capable of passing through the transapical port, to an operative condition in which it assumes a shape which enables it to be navigated through the mitral valve without entanglement in the left ventricular space and sub-valvular apparatus.

In this embodiment, the catheter (152) includes a flexible tubular member (158) which is capable of receiving a fluid therein. In the stowed condition, the tubular member (158) is held within a retractable sheath (159) at the distal end (154) the catheter (152), typically in a deflated, folded condition. Through manipulation of the proximal end (156) of the catheter (152), the sheath (159) may be retracted or advanced to expose the tubular member. A fluid may then be introduced into the tubular member (158) causing it to expand and to extend from its collapsed state. Such manipulation may include the use of a pump, typically in the form of a large bore syringe, to pump the fluid, typically sterile water or a sterile saline solution into the tube. Such pumps are well known in the art and their functioning and use will be apparent to those skilled in the art.

Once the tubular member (158) has fully expanded, it has a partially domed or arrowhead-like shape which, when it bears on a wall of the left ventricle and is advanced towards the mitral valve, causes the distal end (160) of the tubular member (158) to be directed into the mitral valve. The location device (150) of this embodiment thus functions similarly to the location device (100) illustrated in FIGS. 2A and 2B except that in this embodiment the location device (150) expands through inflation, which is often termed balloon expandable, and has a less complex structure.

The embodiment illustrated in FIGS. 3A and 3B preferably also includes pressure sensors (not shown) as described above with reference to FIGS. 2A and 2B.

Once successful navigation through the mitral valve has taken place, orientation within the valve must be accurately assessed. The further embodiments described below are described with reference to transapical procedures but could be used in any other percutaneous entry provided that the operative elements are suitably oriented with respect to the catheter.

Figure 4A:
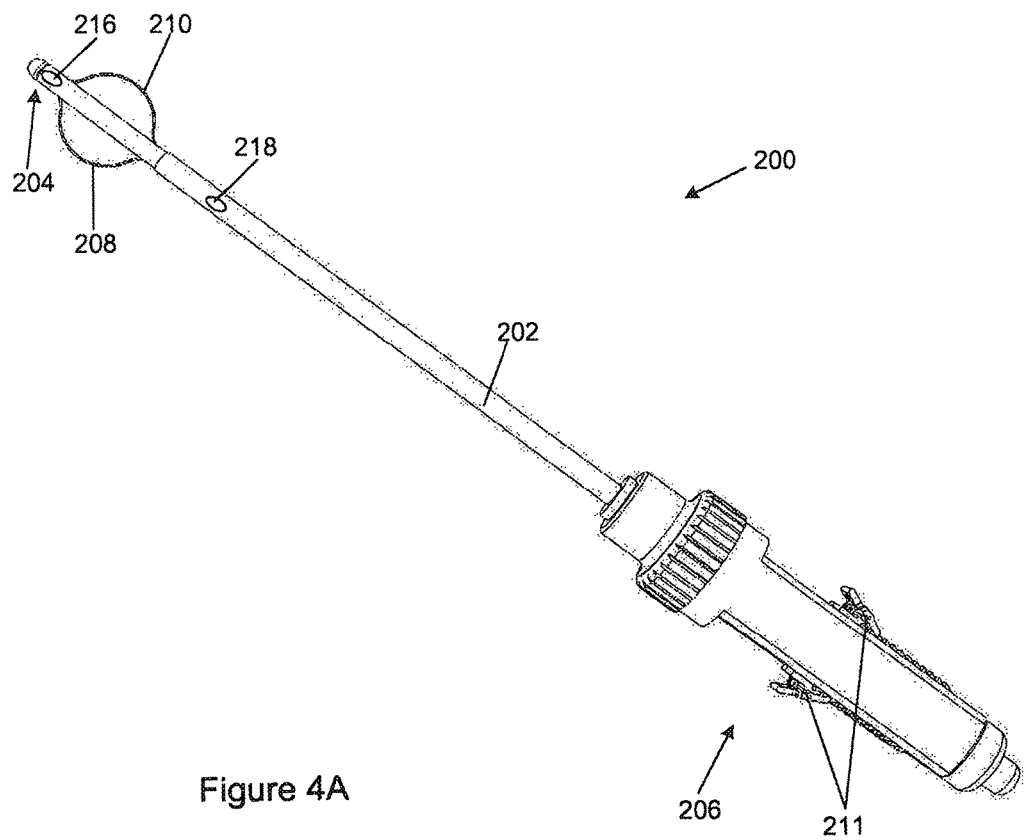
FIGS. 4A and 4B are anterior views of a first embodiment of an orientation device in which the orientation device is in an operative condition and the commissural arms extend outwardly.
Figure 4B:
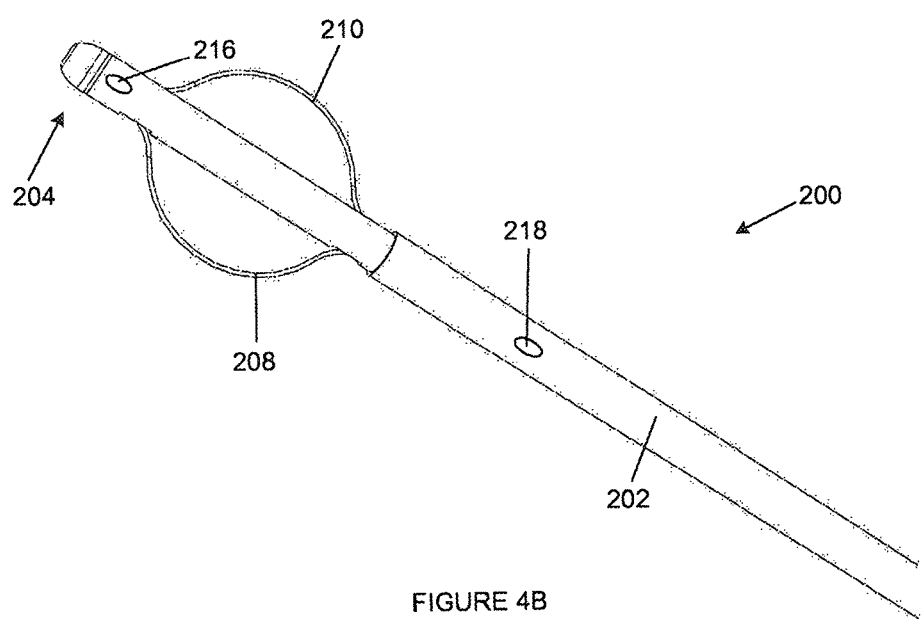

FIGS. 4A and 4B illustrate a first embodiment of an orientation device (200) for use in mitral valve repair surgery and which may be used in conjunction with a location device described above. The orientation device (200) includes a catheter (202) having a distal end (204) configured to enter the heart through a transapical port and through the mitral valve into the left atrium, and a proximal end (206) configured for manipulating the orientation device (200). The orientation device (200) includes two operatively arcuate or bow-like commissural arms (208, 210) adjacent the distal end (204) of the catheter (202) and each of which extend generally within a plane. In this embodiment the plane in which each arm extends is generally co-planar with that of the central axis of the distal end of the catheter (202). Each arm (208, 210) is formed by a flexible elongate member, in this embodiment a nitinol wire, attached at its ends to the catheter (202) and which can be manipulated to move the ends together to cause the members to flex outwardly from the catheter (202) and assume an arcuate shape. The manner in which this is achieved is analogous to that described above in which the flexible elongate members (110) of the location device are operated. However, many other methods of causing the arms (208, 210) to flex outwardly will be apparent to those skilled in the art. Each arm (208, 210) is furthermore individually operable and partially rotatable about the length of the catheter (202).

The commissural arms (208, 210) are configured to be operatively locatable within the mitral valve commissures and may be deployed from a stowed condition, in which the catheter (202) can pass through the transapical port, to an operative condition, in which they extend outwardly on generally opposite sides of the catheter (202) through manipulation of the proximal end (206) thereof. Once the arms (208, 210) have been deployed, they may be individually extended or retracted and rotated to achieve accurate location within the commissures of the mitral valve.

With the arms (208, 210) located within the commissure, rotational movement of the catheter (202) relative to the mitral valve is limited. Importantly, the arms (208, 210) do not occlude the valve.

In this embodiment a linear slider and rotatable knob (211) is provided on the proximal end (206) of the catheter (202) for operating each arm (208, 210), however, any suitable method can be used to operate or manipulate the arms (208, 210).

Figures 5A, 5B:
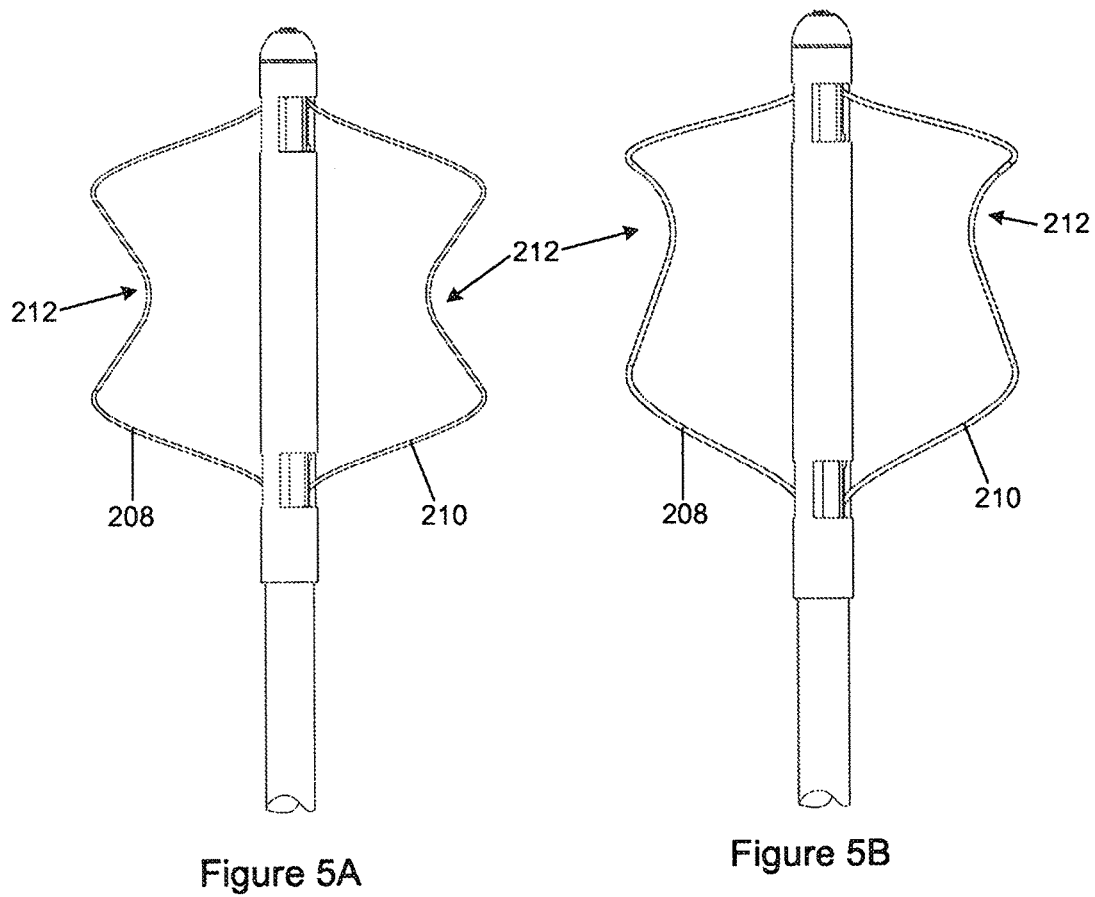
FIGS. 5A and 5B are anterior views of alternative embodiments of the orientation device illustrated in FIGS. 4A and 4B.

Referring FIGS. 5A and 5B, each arm (208, 210) may include an indentation (212) along its length which is shaped to extend partially about a valve commissure, at the level of the valve annulus, and thus limit axial movement of the device (200) relative to the valve. The indentations (212) operatively extend about or over the commissures from the ventricle to the atrium. These indentations can be formed using the shape memory aspect of the nitinol, which is a superelastic, shape memory nickel titanium alloy.

Once the commissural arms (208, 210) have been successfully located within the mitral valve commissures with the indentations (212) extending partially about the valve commissures, the function to limit rotational movement of the catheter (202) relative to the mitral valve without affecting the function of said valve, and also limit axial movement of the catheter (202) with respect to the mitral annulus. This primarily functions to allow further diagnostic and therapeutic procedures to be carried out in a reliable, repeatable manner. This further ensures that the device (200) cannot accidentally either be pushed further into the left atrium or withdrawn therefrom.

Furthermore, in order to assist in locating the arms (208, 210) within the valve commissures, the orientation device (200) includes two pressure nodes or sensors (216, 218) on the catheter (202), one adjacent each end of the arms (208, 210). The pressure nodes (216, 218) are substantially identical to those described above with reference to FIGS. 2A and 2B and can be used to measure the transvalvular pressure in the same manner. Also, pressure measurements prior to deployment of the arms (216, 218) can be compared to measurements after deployment. Where the pressure readings are the same or substantially similar, the arms (216, 218) will have been successfully located within the commissures. On the other hand, pressure readings that are significantly different signify that the arms (216, 218) are not located in the commissures and are preventing the valve leaflets from closing properly and causing regurgitation. In other words, a pressure reading that is significantly different to those readings prior to deployment signifies that the arms are located at an angle oblique to the line of coaptation of the valve leaflets and are thus preventing the valve leaflets from closing properly and causing regurgitation. Substantially similar readings will typically be those which differ by less than 10%, preferably less than 5%, most preferably less than 1% and will be apparent to a surgeon skilled in the art.

Figure 6A:
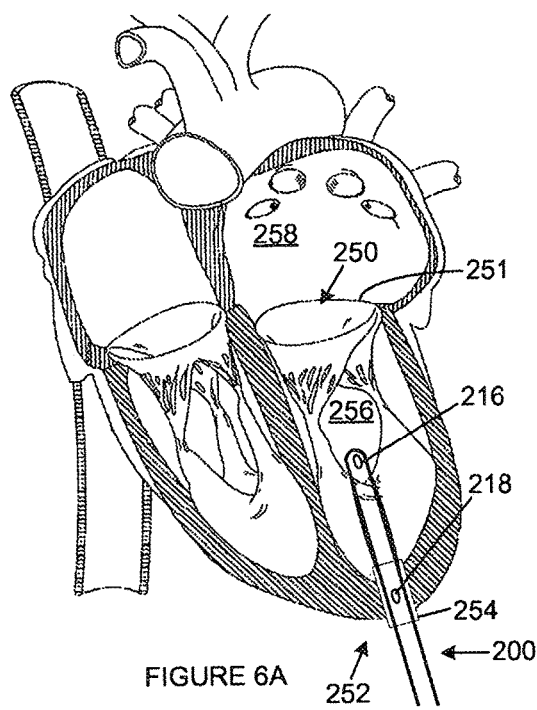
FIGS. 6A to 6D are schematic drawings illustrating the orientation device of FIG. 5A being used within a mitral valve.

FIGS. 6A to 6D illustrate the manner in which the orientation device (200) of FIG. 5A is used to determine the orientation of the mitral valve (250). The orientation device (200) is inserted into the heart at the heart's apex (252) through the transapical port (254). FIG. 6A illustrates the orientation device (200) entering the heart in a stowed condition, whereafter it is navigated through the mitral valve (250). Navigation through the mitral valve (250) may take place by advancing the distal end (204) of the catheter (202) in the direction of the mitral valve (250). Alternatively the device could also include a location device (150) as disclosed in FIGS. 2A and 2B or FIGS. 3A and 3B. Further alternatively, the device (200) could be used in conjunction with a location device described above. The location device (150) could be deployed from the distal end (204) of the catheter (202) which can then be navigated through the mitral valve (250) by advancing the location device (150) through the ventricle (256). As the location device (150) is shaped such that it bears on a surface of the left ventricle (256), the distal end (204) of the catheter (202) will be advanced through the mitral valve (250) and into the left atrium (258).

The pressure sensors (216, 218) will indicate once the device has been successfully navigated into the left atrium (258), as the first pressure sensor (216) will indicate atrial pressure, while the second pressure sensor (218) will indicate ventricular pressure, as described with reference to FIGS. 2A and 2B.

Figure 6B:
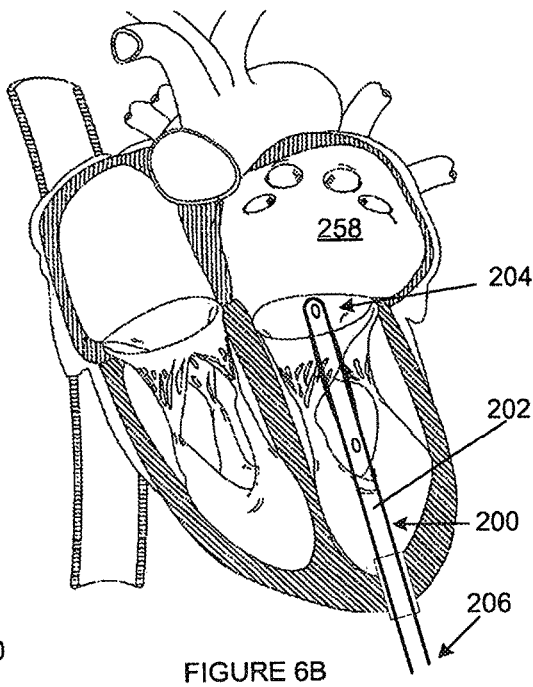
Figure 6C:
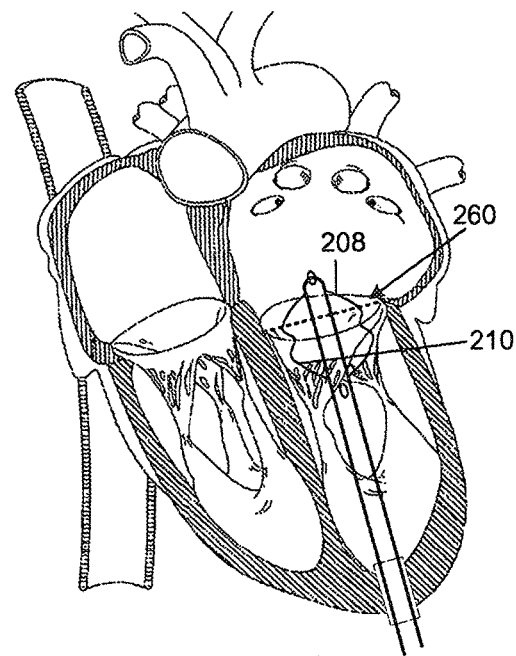

Once the distal end (204) of the catheter (202) has successfully been navigated through the mitral valve (250), as illustrated in FIG. 6B, the proximal end (206) of the catheter (202) is manipulated using pull and/or push wires or other actuation methods apparent to those skilled in the art causing the commissural arms (208, 210) to be partially deployed, such that they flex and extend outwardly on opposite sides of the catheter (202), as is illustrated in FIG. 6C.

Figures 7A, 7B:
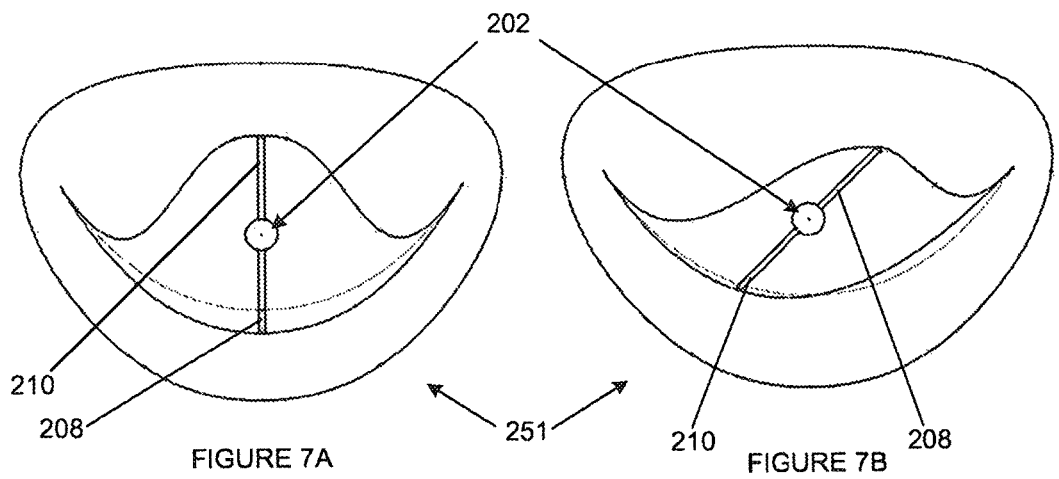
FIGS. 7A to 7E are schematic atrial views illustrating the orientation device of FIG. 5A being used within a mitral valve.

In FIG. 6C, and also referring to FIGS. 7A and 7B, the commissural arms (208, 210) of the orientation device (200) are deployed at an angle to the line of coaptation (260) of the mitral valve (250). This prevents the valve (250) from closing properly and thus causes regurgitation which will in turn cause the transvalvular pressure to be different, typically lower, to that which will have been measured prior to deployment of the arms (208, 210). This indicates that the commissural arms (208, 210) are preventing the valve (250) from closing properly and that the orientation device (200) must be rotated to a different position. Thus the arms (208, 210) are returned to their stowed condition, the device (200) is rotated, the arms (208, 210) deployed again and pressure measured and compared to the initial measurements. This procedure is repeated until the transvalvular pressure measurement prior to deployment is substantially similar to the measurement after deployment, which will indicate that the valve (250) can function properly and that the commissural arms (208, 210) are deployed within the line of coaptation (260) of the valve (250) and hence the arms (208, 210) are oriented such that they are deployed or located in the commissures of the valve (250) without significantly affecting valve function.

It is not necessary to compare pressure measurements to the corresponding initial pressure measurements in both the atrium (258) and ventricle (256). Preventing normal operation of the valve (250) will affect the pressure in both the atrium (258) and ventricle (256). Pressure will increase in the atrium and decrease in the ventricle, thus it is only required to compare the pressure in either the ventricle or the atrium to the initial pressure in the corresponding chamber. Alternatively the pressure difference across the valve can be measured. A lower pressure difference indicates regurgitation caused by the arms (208, 210) preventing the valve (250) from closing properly or in its normal fashion.

Hereafter, the commissural arms (208, 210) can be individually expanded and rotated about the catheter (202) until they locate within the respective valve (250) commissures (262). This will again be apparent from an improved pressure measurement in either or both chambers.

Figure 6D:
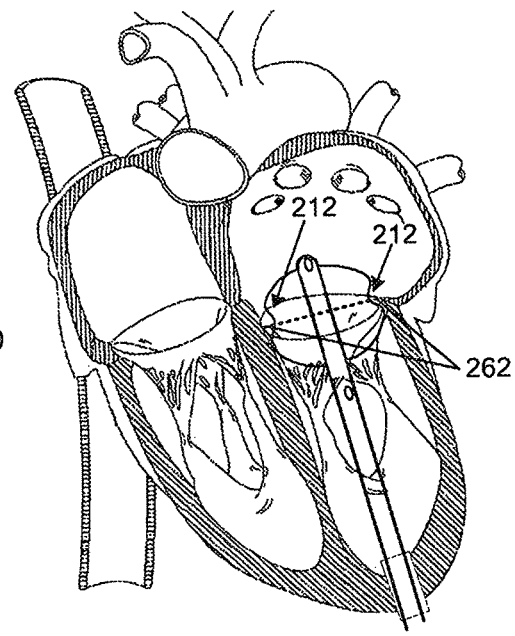

The device (200) is then moved axially until the indentations (212) in the commissural arms (208, 210) extend about the mitral valve commissures (262) at the level of the valve annulus, as is illustrated in FIG. 6D. The surgeon is able to determine this through tactile feedback and confirm the transmitral position using pressure feedback. At this stage the device (200) will have been successfully orientated within the mitral valve (250) and the arms (208, 210) are fully expanded. Axial movement of the device (200) relative to the mitral annulus (and thus the valve (250)) will in consequence be limited.

It will be appreciated that positioning of the device (200) by means of the pressure nodes (216, 218) and the two commissural arms (208, 210) allows the device to be orientated within the mitral valve annulus (251) with regard to the axial (12) as well as rotation about said axis.

In addition to locating the orientation device (200) within the mitral valve annulus (251) with regard to axial and rotation about the said axis, it is desirable that the device (200) be correctly orientated within the mitral valve annulus (251) with regard to the antero-posterior axis (20). This is illustrated in FIGS. 7C and 7D.

Figure 7C:
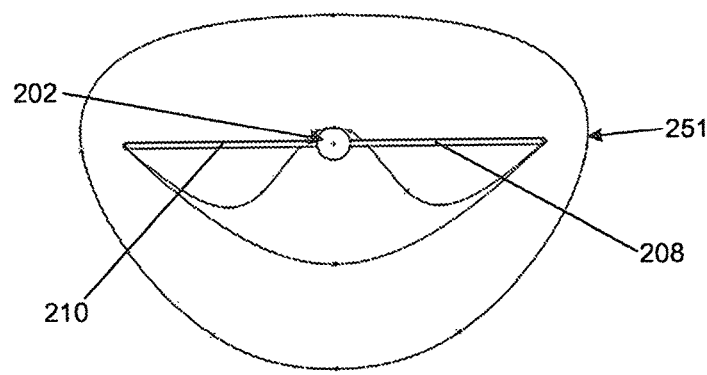
Figures 7D, 7E:
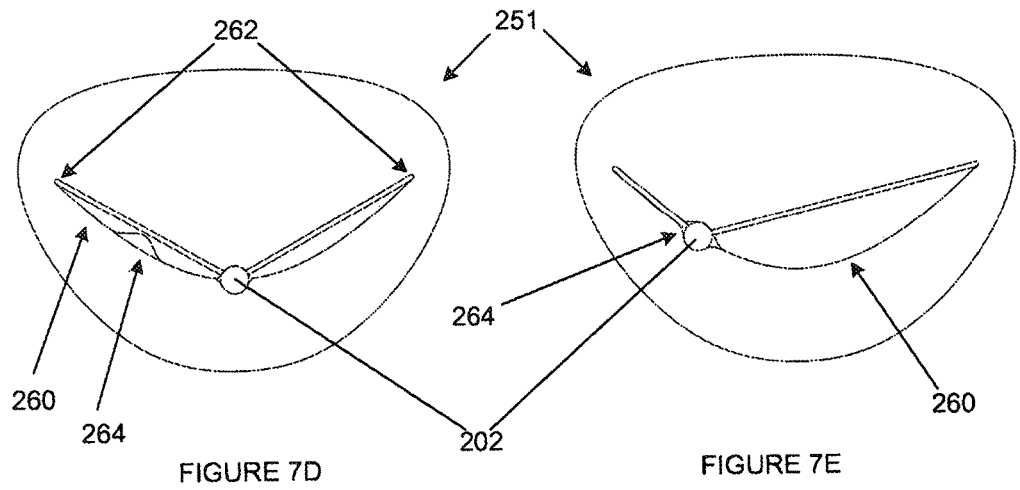

The line of coaptation of the mitral valve (260) is not a straight line but rather arc shaped as indicated in FIGS. 7D and 7E. Thus the commissures (262) do not lie in a straight line from the centre of the valve annulus (251) and the commissural arms (208, 210) are required to be partly rotatable about the catheter (202). In this manner the catheter (202) can be moved in an antero-posterior direction by rotating the commissural arms (208, 210).

Orientation of the catheter (202) within the line of coaptation (260) with regard to the antero-posterior degree of freedom is illustrated in FIGS. 7C and 7D. As the commissural arms (208, 210) are rotated, causing the catheter (202) to move, the pressures within the atrium (258) and ventricle (256) are measured. Where a pressure reading is achieved indicating pressures substantially similar to those prior to deployment within the two chambers, the catheter (202) will have been correctly orientated with regard to the antero-posterior degree of freedom as illustrated in FIG. 7D.

Furthermore, it is common that the zone of regurgitation (264) does not occur at the centre of the line of coaptation (260), but rather offset from the centre as illustrated in FIGS. 7D and 7E. In order to correctly position the transmitral portion of the catheter (202) within the zone of regurgitation (264), the two commissural arms (208, 210) are individually flexed to either extend or retract them, thus moving the catheter (202) with regard to the mediolateral degree (16) of freedom. Orientation of the device (200) mediolaterally is illustrated in FIG. 7E.

The catheter (202) can thus be moved within the mitral valve between the commissures (262) while the arms (208, 210) are located in the commissures (262). As indicated, this is achieved by extending one arm while simultaneously retracting the other arm. The catheter (202) then acts as a transmitral rod which can be moved into a jet or zone of regurgitation (264) in the valve (250) to block or monitor the jet or zone of regurgitation (264). Such jets or zones of regurgitation (264) result from incompetencies in the valve (250) and are typically the cause of the problem the surgery seeks to cure. Once the jet has been located in this way, a repair procedure can then be carried out at this position.

It will be apparent to a surgeon when the catheter (202) has been successfully moved into a jet as pressure measurements will show an improvement. Such improvement will be evidenced by a higher pressure in the ventricle and a lower pressure in the atrium in consequence of flow of blood from the ventricle to the atrium, or regurgitation, being restricted or eliminated.

It will be appreciated that once the commissural arms (208, 210) of the orientation device (200) have been properly deployed within the mitral valve commissures (262), and the catheter (202) has been moved relative thereto through rotation and/or expansion or flexing of the commissural arms (208, 210), the device (200) will have been correctly orientated, and will be limited from movement with regard to the axial, rotation about the axial, antero-posterior, and mediolateral degrees of freedom. Nevertheless, the device (200) will still be free to rotate about antero-posterior axis as well as the mediolateral axis.

Figure 8:
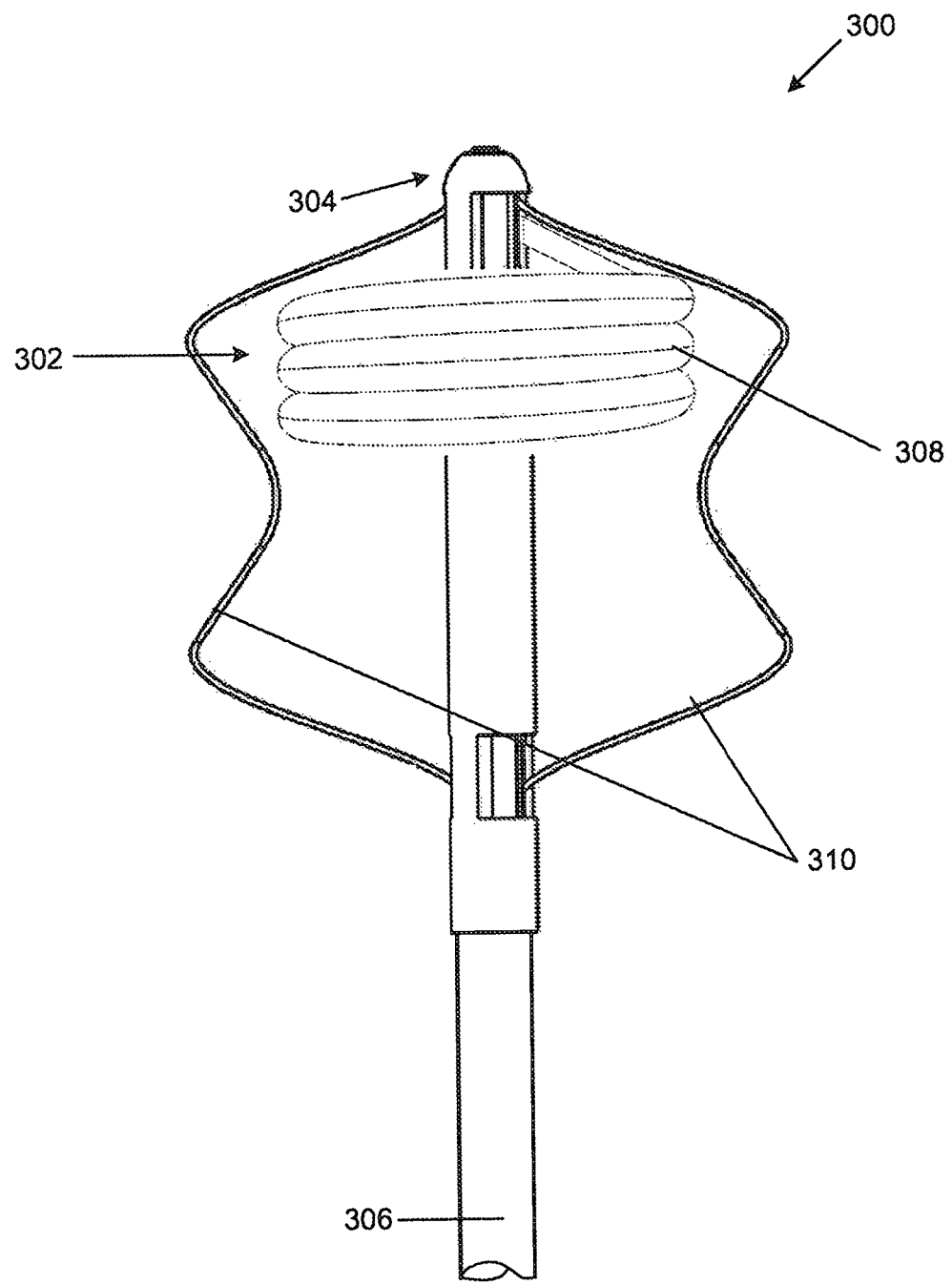
FIG. 8 is an anterior view of an alternative embodiment of the orientation device illustrated in FIG. 5A, in which an atrial anchor is associated with the distal end of the device and is shown in its operative condition.
Figures 9, 10:
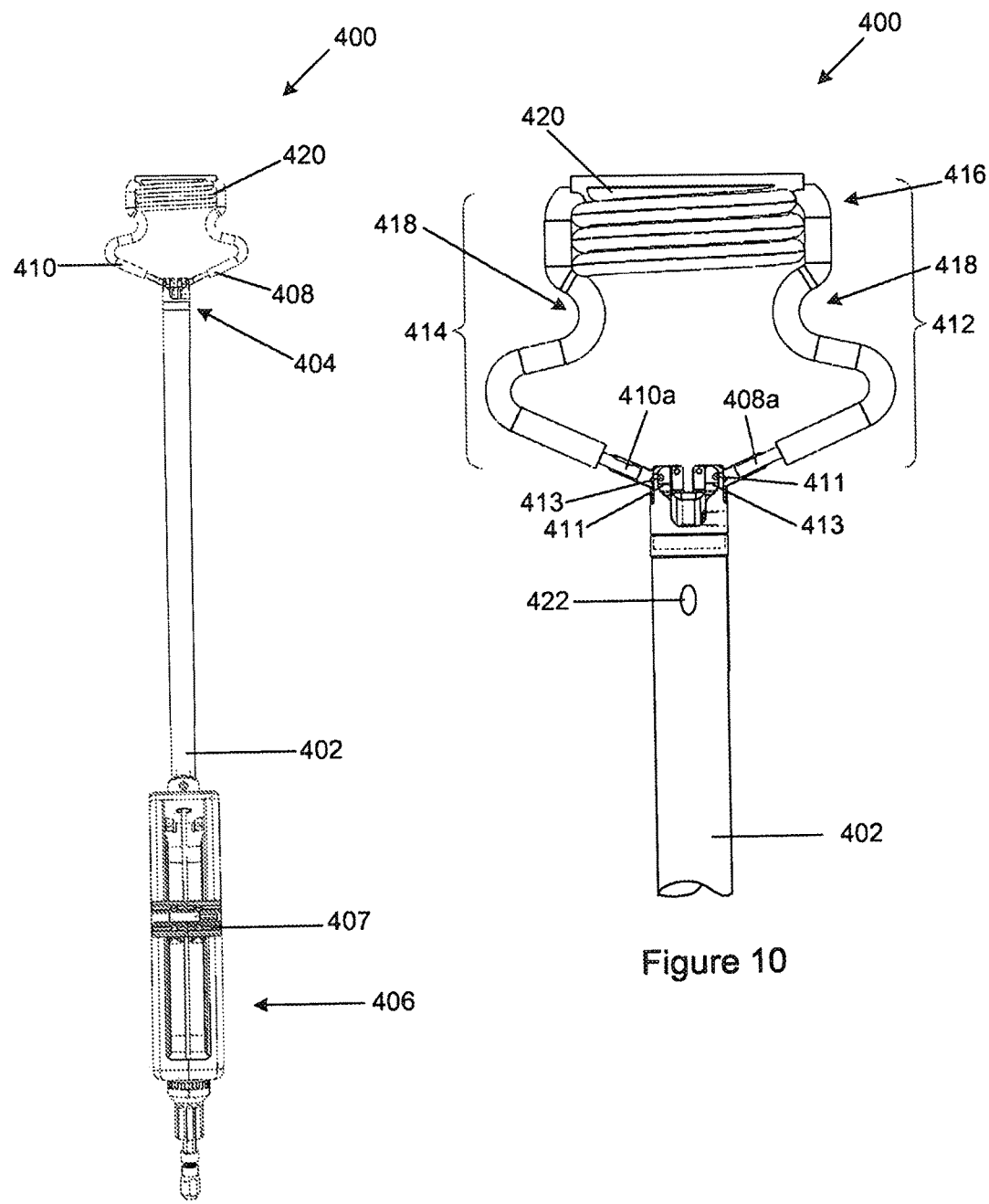
FIG. 9 is an anterior view of an alternative embodiment of an orientation device.
FIG. 10 is a further anterior view of part of the orientation device in FIG. 9
Figure 14:
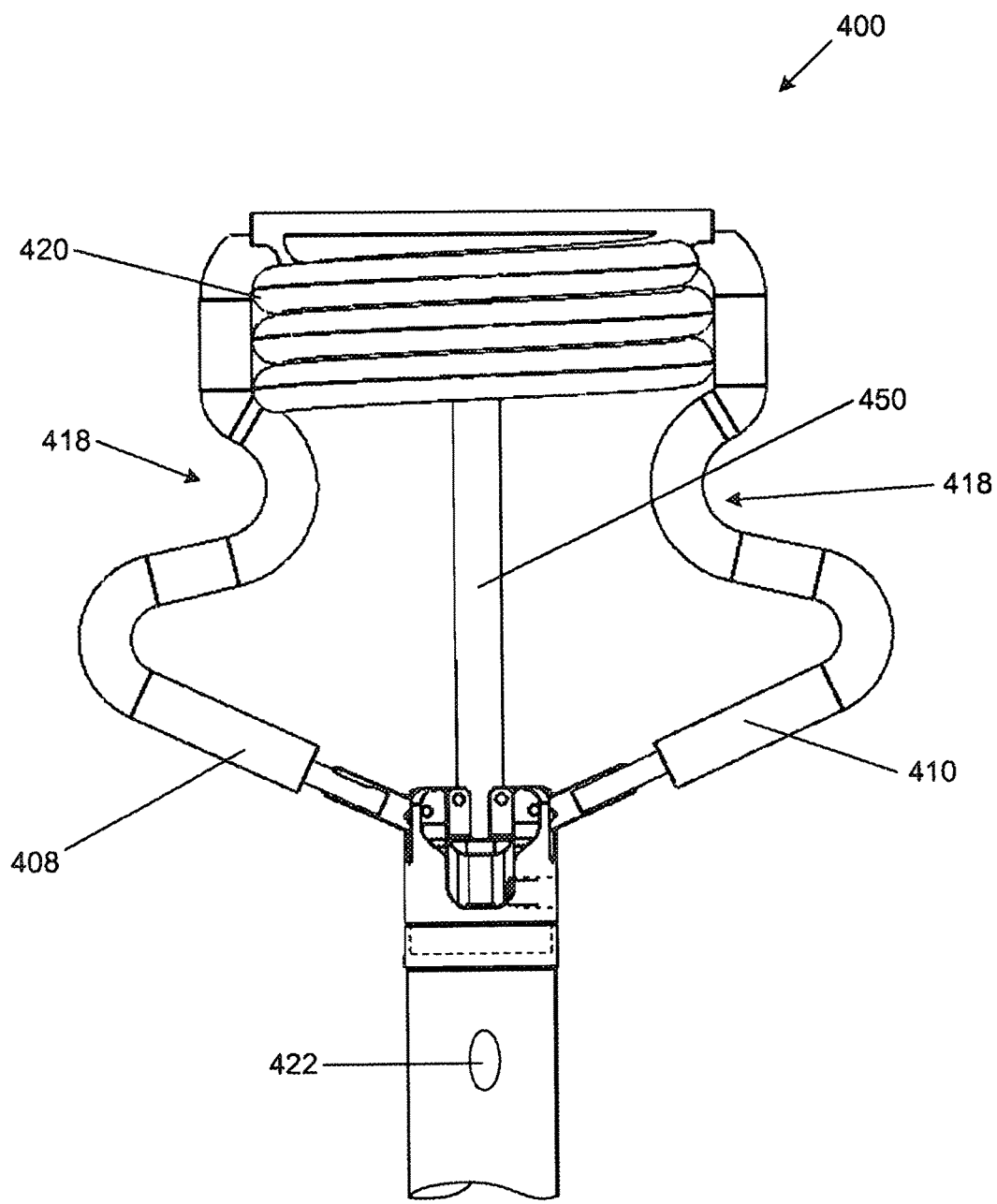
FIG. 14 is an anterior view of the location device in FIG. 9 in which a probe extends from the catheter.
Figure 15A:
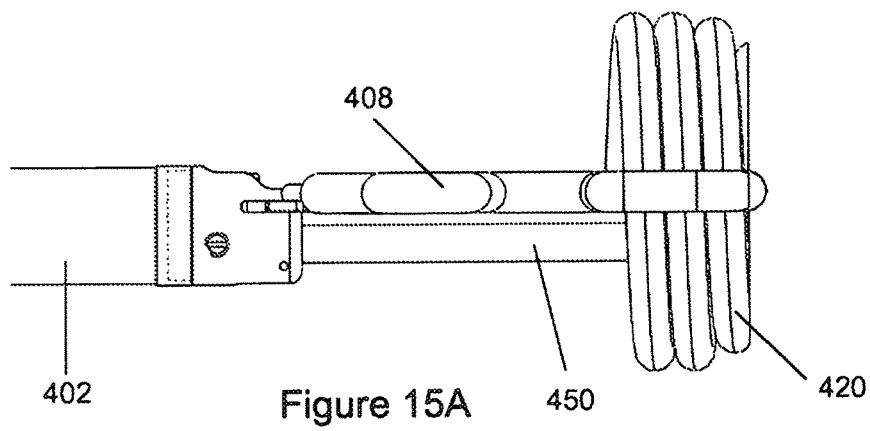
FIGS. 15A to 15C are medio-lateral views of the orientation device in FIG. 14 with the probe bent in varying degrees.
Figure 15B:
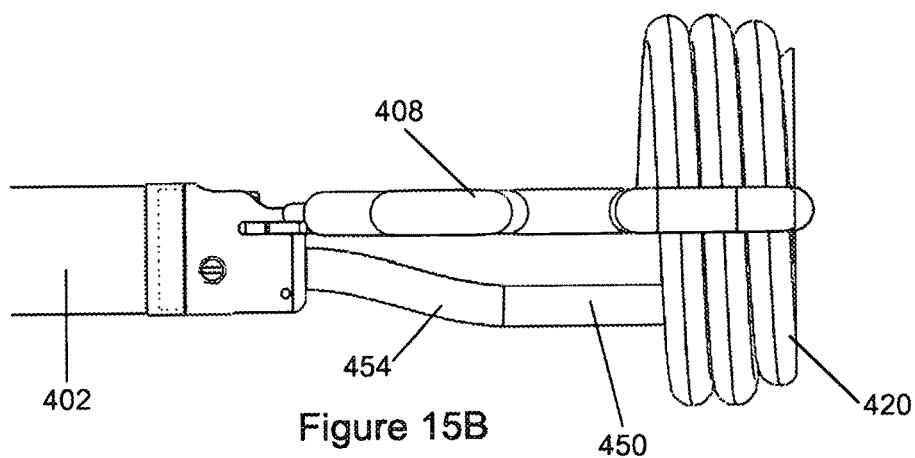
Figure 15C:
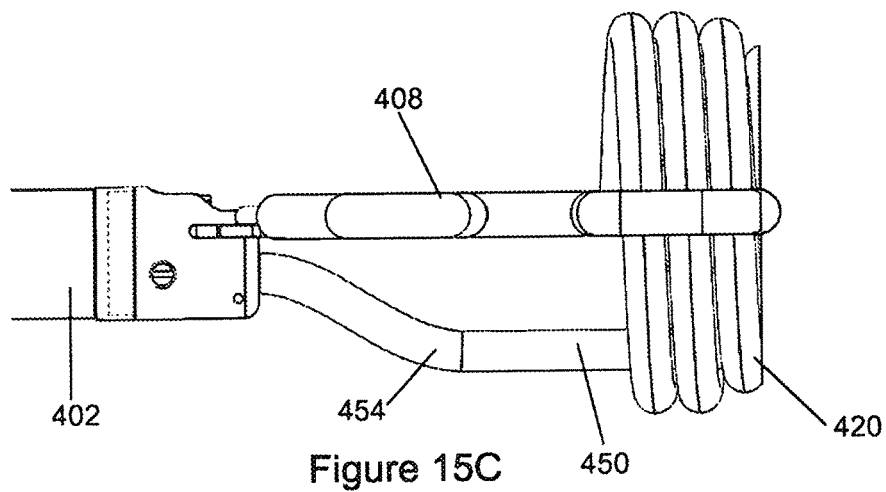
Figure 16A:
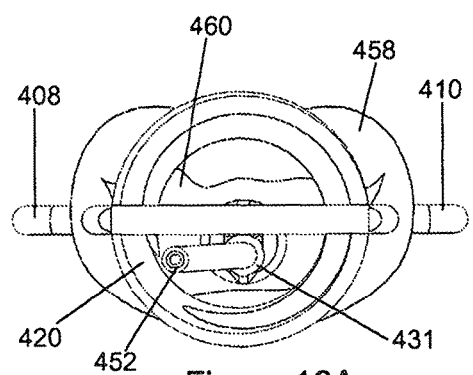
FIG. 16A to 16E are part-sectional atrial views of the orientation device in FIG. 14 in use with a mitral valve.
Figure 16B:
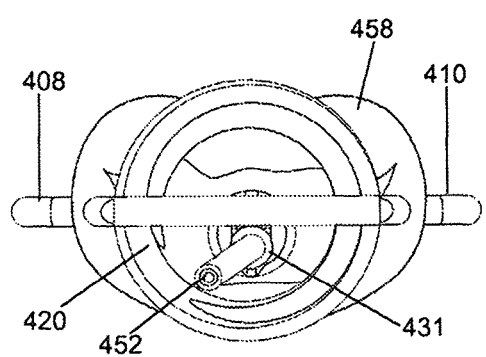
Figure 16C:
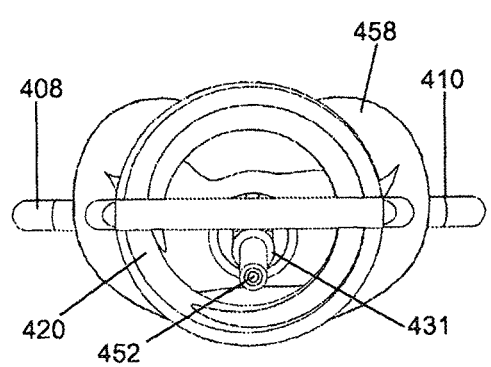
Figure 16D:
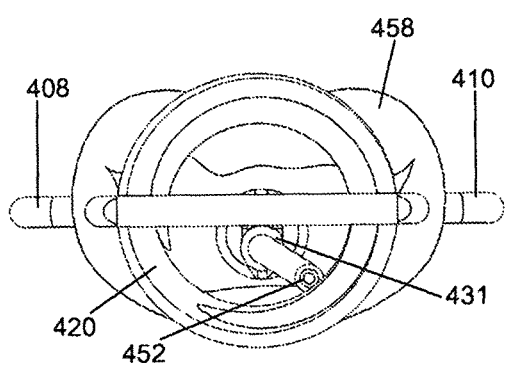
Figure 16E:
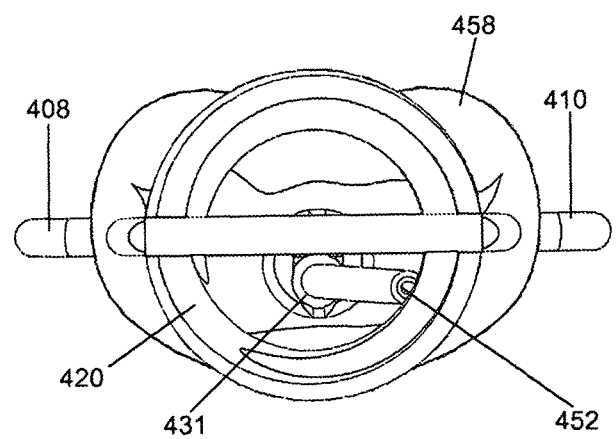

A further embodiment of an orientation device (300) is illustrated in FIG. 8 which is configured to limit rotation of the device about antero-posterior and the mediolateral axes. The orientation device (300) illustrated is substantially identical to the device (200) illustrated in FIG. 5A, except that device has an atrial anchor (302) associated with the distal end (304) of the catheter (306). The atrial anchor (302) can be deployed from an stowed condition, in which it is stored within the catheter (306) and thus permits the catheter (306) to pass through the transapical port and into the left atrium, to an operative condition, in which it extends from the catheter (306) and forms a looped or annular shape within the commissural arms (310) which is locatable in or over the mitral valve annuls. In the embodiment illustrated, the anchor (302) is formed by a tubular member (308) made of a flexible material which can receive a fluid therein. This enables the anchor (302) to be expanded in balloon fashion from its stowed condition, in which it is collapsed onto itself, to its operative condition in which it is looped to form a helix with the longitudinal axis of the helix generally corresponding to that of the catheter (306).

Once the atrial anchor (302) has been deployed in the left atrium it locates over the mitral valve annulus and cannot be withdrawn or pass through the mitral valve without first being deflated. This not only provides an additional safeguard against the accidental removal or withdrawal of the orientation device (300) from the mitral valve, but also provides a reference axis for axial and angular orientation as it provides a rigid structure which is resistant to lateral movement or distortion. In addition, as the anchor (302) is annular in shape and locates above the mitral valve annulus, it limits rotation of the device (300) about the antero-posterior and mediolateral axes. Importantly, its annular shape also permits of substantially normal blood flow.

Deployment of the anchor (302) may take place even before the commissural arms (310) of the orientation device (300) have been deployed or located within the mitral valve commissures.

Although any suitable annular shape may function to limit the rotational movement of the device (300), it is preferred to use a helically shaped anchor (302) as the helical configuration provides additional column strength to the anchor (302). This is particularly important where the anchor (302) is provided by a tubular member which is expanded, similar to a balloon. A simple ring or loop shape may not be sufficiently rigid and may tend to collapse onto itself when sufficient force is exerted thereon.

It will further be appreciated that the atrial anchor (302) and a spearhead-shaped location device (150) as illustrated in FIGS. 3A and 3B could be integrally formed by a tubular member, such that partial expansion of the tubular member causes only the location device to deploy and expand outwardly from the catheter. The location device could then be utilized to navigate into the left atrium after which the tubular member could be further expanded so as to deploy the atrial anchor within the left atrium. At this stage the commissural arms could be deployed to then successfully locate the catheter within the zone of regurgitation as described above.

The commissural arms could also be manufactured from a shape memory alloy, such as nitinol, which has been pre-formed to the desired arcuate shape and which are held in a deformed, relatively unbent shape during entry of the device into the heart, and which are permitted to return to their pre-formed bent shape through manipulation of the device from its stowed condition to its operative condition.

FIGS. 9 to 13 illustrate yet a further alternative embodiment of an orientation device (400). The device includes a catheter (402) having a distal end (404) which is configured to enter the heart through a transapical port and through the mitral valve into the left atrium, and a proximal end (406) which is suitably configured for manipulating the orientation device (400). The orientation device (400) further includes two generally arcuate commissural arms (408, 410). Each arm (408, 410) is pivotably secured at one end (413) to the distal end (404) of the catheter (402), in this embodiment offset from its centre, and capable of pivoting relative thereto. In this embodiment the arms (408, 410) are independently pivotable, each being capable of manipulation through a push rod (411) extending from a slider (407) on the proximal end (406) of the device (400). A helical atrial anchor (420) is located centrally between the arms (408, 410) opposite the catheter (402).

The commissural arms (408, 410) are tubular so as to be capable of receiving a fluid therein from a pump (not shown) at the proximal end (406) of the catheter (402). The pump typically resembles a syringe and is filled with an incompressible fluid such as sterile water. Part (412, 414) of each arm (408, 410) is made from a flexible material such that the parts (412, 414) may be inflated, balloon style, during deployment thereof. For structural strength, a rigid metal tube forms the end (408a, 410a) of each arm adjacent its pivot (413) on the distal end (404) of the catheter (402). The flexible material is, in this embodiment, laser welded to the metal tube.

Also in this embodiment, the arms (408, 410) are connected to each other such that the tubular material forms a continuous loop (416). The flexible tubular material further defines in its length an atrial anchor (420) between the arms (408, 410) as is described in greater detail below.

Prior to being deployed, the arms (408, 410) and atrial anchor (420) are stowed within a retractable sheath (430) provided over the distal end of the catheter, as shown in FIG. 11. In the stowed condition the rigid tube of each arm extends in the length of the catheter while the flexible tube is in a collapsed state and folded within the sheath (430). In this condition the catheter (402) can pass through the transapical port.

The arms (408, 410) and atrial anchor (420) can be deployed from the stowed condition by inflating them with a fluid. Once fully inflated in the operative condition, the arms (408, 410) extend outwardly from the catheter in opposite directions to each other, each extending generally within a plane. In this embodiment the plane in which each arm extends is generally parallel to that of the central axis of the distal end (404) of the catheter (402). The arms (408, 410) are outwardly inclined from their ends (408a, 410a) adjacent the tip of the catheter (402) whereafter each arm (408, 410) is shaped to form an inwardly extending indentation (418) along its length.

Hereafter the tubular member forms the atrial anchor (420) which has a helical shape and is substantially similar to the atrial anchor described with reference to FIG. 8. The helically extending coils or loops of the tubular member follow a shallow pitch and abut each other to provide a substantially solid annular cylinder or tubular shape when inflated. The diameter of the helix is selected to approximate that of the mitral valve annulus so that the atrial anchor (420) can locate on the mitral valve annulus.

In the operative condition the arms (408, 410) are able to extend into the mitral valve commissures. The indentation (418) on each arm is shaped to extend partially about a valve commissure and thus limit movement of the device (400) relative to the valve once fully deployed. Once the commissural arms (408, 410) have been successfully located within the mitral valve commissures, and the indentations (418) extend about the commissures, axial movement of the device (400) is substantially limited.

Each arm (408, 410) can be individually pivoted within the plane in which it extends, or the arms (408, 410) simultaneously pivoted, with respect to the catheter (402), and hence in relation to the other, to assist in locating the arms (408, 410) within the valve commissures and more particularly to locate the indentations (418) about the valve commissure. The surgeon is able to assess when the indentations are properly located about the valve commissures by tactile feedback received on the proximal end of the catheter in reaction to both axial movement and rotational movement of the catheter (402).

In use the distal end (404) of the catheter (402) is advanced into the left ventricle through a transapical port with the commissural arms (408, 410) and atrial anchor (420) in the stowed condition within the sheath (430) at the distal end (404) of the catheter (402). A pressure reading is taken using the pressure node (422) on the catheter (402) adjacent its distal end (404). The catheter (402) is then further advanced through the mitral valve, this being indicated by further pressure readings. A lower pressure reading indicates that the distal end is in the left atrium. At this stage the commissural arms (408, 410) and atrial anchor (420) are inflated using the pump (not shown) at the proximal end (406) of the catheter (402). With the ends (408a, 410a) of the arms pivoted towards each other and extending generally in the direction of the longitudinal axis of the catheter (402), the catheter (402) is withdrawn through the mitral valve until the atrial anchor (420) locates in the mitral valve annulus. In this position further withdrawal is not possible as the expanded atrial anchor (420) is too large to fit through the mitral valve. With the atrial anchor (420) in this position a uniaxial reference is created without valve function being affected.

At this point, the position of the commissural arms (408, 410) within the mitral valve is unknown and must be established. This is achieved substantially as described above with reference to FIGS. 6C and 6D and FIGS. 7A to 7D.

In this embodiment the inflated commissural arms (408, 410) are rotated, with their ends (408a, 410a) pivoted towards each other, within the mitral valve by rotating the proximal end (406) of the catheter (402). Pressure readings are simultaneously taken. The position of the commissural arms (408, 410) in which the pressure measurement corresponds most closely to the initial pressure measurement will be that in which the arms have the least effect on coaptation of the mitral valve leaflets. This position is that in which the plane in which the commissural arms (408, 410) extend corresponds most closely to the line of coaptation of the mitral valve. To assist in finding this position, the arms (408, 410) can be rotated in a step-wise fashion and the arms (408, 410) pivoted away from each other after each rotation. The pressure can then be measured before the arms (408, 410) are again pivoted towards each other and the device (400) is rotated to the next position. This procedure is repeated until the pressure readings are approximately similar to the initial pressure reading, indicating that the arms (408, 410) are located within the line of coaptation of the valve.

Once the position has been established in which the commissural arms (408, 410) extend in the line of coaptation of the mitral valve the arms (408, 410) are moved further apart, by pivoting their ends (408a, 410a) further apart, to extend into the mitral valve commissures. Hereafter the indentations (418) in the arms (408, 410) are located about the commissures by manipulation of the proximal end (406) of the catheter (402) in the axial direction. Tactile feedback on the catheter (402) will indicate to the surgeon when this has been achieved. Once the indentations are located over the mitral valve commissures the ends (408a, 410a) of the commissural arms (408, 410) are pivoted fully apart, locking them in position within the mitral valve. With the commissural arms (408, 410) locked in position within the mitral valve commissures, axial movement and rotation about the axis of the device (400) is prevented. Also in this condition, the atrial anchor (420) is located within the mitral valve annulus and prevents mediolateral and antero-posterior movement as well as rotation of the device (400) about these axes. Thus movement of the device in all six degrees of freedom is prevented and a stable platform provided which can be used to accurately map the mitral valve. Furthermore, the shape and configuration of the atrial anchor and commissural arms do not occlude blood flow to any significant extent.

Figure 17:
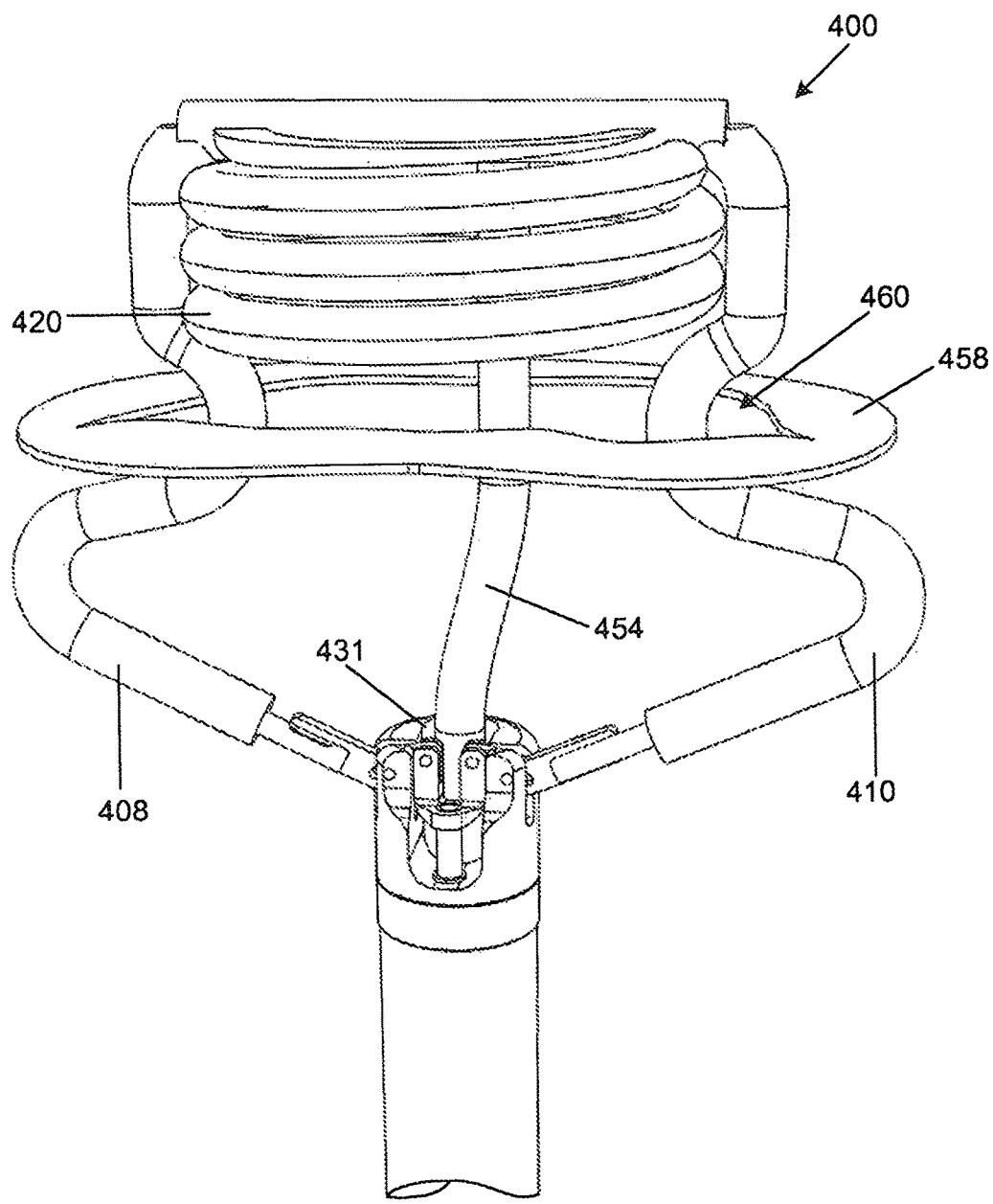
FIG. 17 is a part-sectional three-dimensional view of part of the orientation device in FIG. 14 in use in a mitral valve.
Figure 18A:
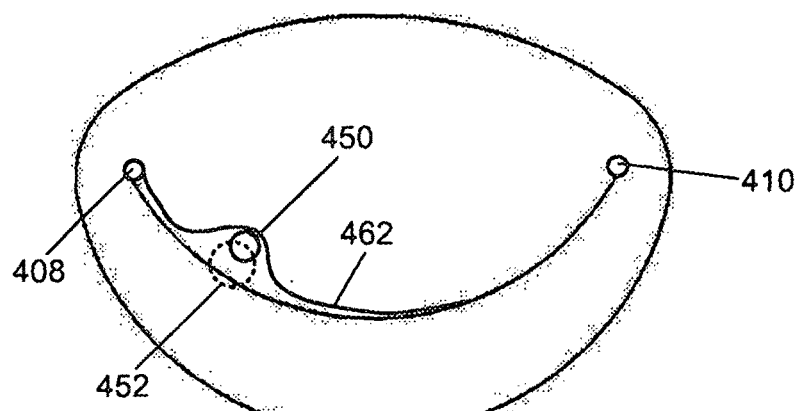
FIGS. 18A to 18C are schematic atrial views illustrating the probe in FIG. 14 being used within a mitral valve.
Figure 18B:
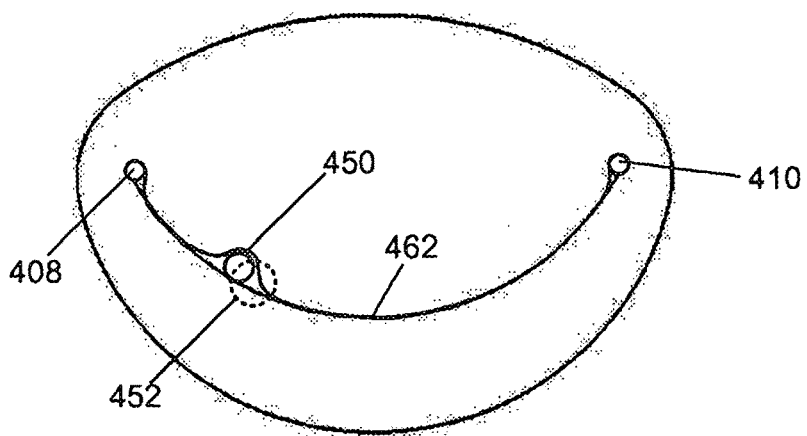
Figure 18C:
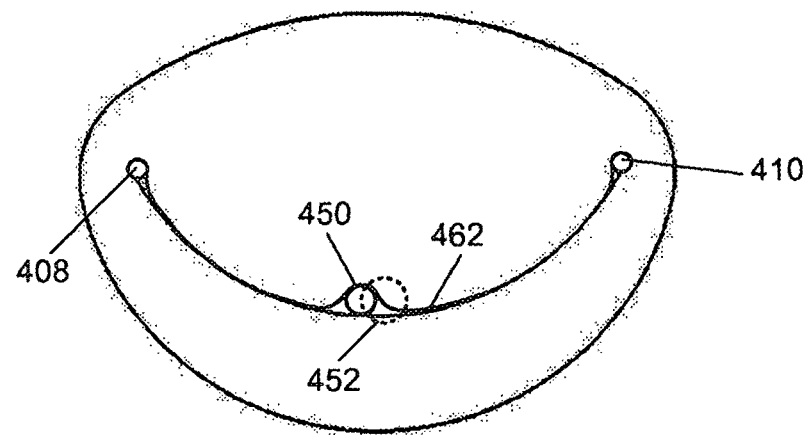

As shown in FIGS. 14 to 17 the device (400) further includes a probe (450) which is stowed centrally within the catheter (402) and which is operatively extended from the distal end (404) through a lumen (431) in the catheter (402) by manipulating the proximal end (406) of the catheter (402). The lumen (431) is best illustrated in FIG. 17. The probe (450) is elongate with a cylindrical, rod-like shape and a rounded tip (452) and in the operative condition extends into the zone of coaptation of the mitral valve. It is movable independently to the commissural arms (408, 410) which act as a fixed reference. The probe (450) can be moved laterally between the commissural arms and can also be bent at two positions along its length to provide a step or shoulder (454) partway along its length and intermediate the indentations (418) and distal end (404) of the catheter (402) to enable the free end of the probe to be displaced radially from the catheter while maintaining a perpendicular position relative to the plane of the mitral annulus. The shoulder (454) is provided proximal to the valve so as to maintain the perpendicular end portion of the probe interacting with the valve. The probe (450) can furthermore be rotated and doing so whilst in a bent configuration permits the probe (450) to follow the curve or path of the line of coaptation. This feature also permits the probe, if desired, to operatively displace a valve leaflet away from the zone of coaptation when the probe interferes with the leaflet.

In use, the probe (450) can be used to explore the mitral valve (458). With the commissural arms (408, 410) and atrial anchor (420) locked in position in the mitral valve as described above, pressure measurements are taken using the pressure node (422). Referring particularly to FIGS. 16A to 16E and FIG. 17, the probe (450) is then extended through the zone of coaptation (460) so that the tip (452) extends partially into the atrium and into the annulus of the atrial anchor (420). Starting preferably with the probe (450) abutting one commissural arm (408, 410), it is moved incrementally towards the opposite arm. The aim is to move the probe (450) centrally within and along the zone of coaptation. In doing so, the probe (450) can act as a transmitral rod which will block or plug a jet or zone of regurgitation in the valve, which results from incompetencies, when it is moved into the jet. Once the jet has been located in this way, a repair procedure can then be carried out at this position.

Figure 19:
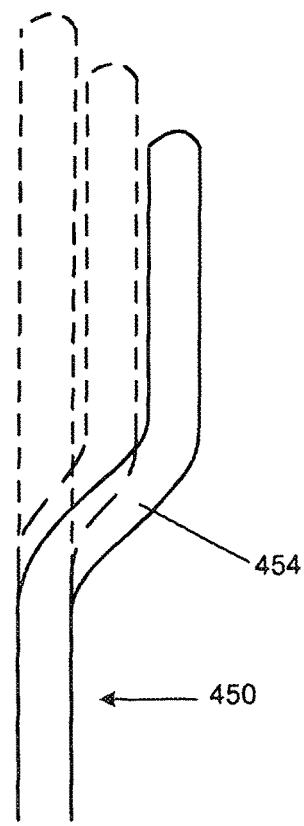
FIG. 19 is a schematic illustration of the bending of the probe of the orientation device in FIG. 14.

The method by which the position of the probe (450) with respect to the zone of coaptation is determined is analogous to that of positioning the commissural arms (408, 410) and is illustrated in FIGS. 16A to 16E and FIGS. 18A to 18C. Pressure measurements are taken and the probe (450) moved in consequence until the pressure is substantially the same as the initial measurements, that is the pressure prior to insertion of the probe (450). This is conveniently achieved by rotating the bent probe (450) at each of a plurality of lateral or radial positions. At each radial position between the commissural arms (408, 410) the probe (450) is thus rotated causing the end thereof after the bend to describe a circle (452) (shown in FIGS. 18A to 18C) which will intersect the line of coaptation (462) at two points. At the points of intersection the probe will lie within the line of coaptation and will not affect the functioning of the valve to any significant extent. Outside of these points the probe will displace the valve leaflets resulting in some regurgitation. Pressure measurements indicate when this occurs and when the probe is in the line of coaptation. Displacement of the leaflets can be increased or exaggerated by increasing the radial displacement of the shoulder (454), for example by increasing its inclination or the severity of the bends as illustrated in FIG. 19, thus making it easier to note a pressure difference.

Furthermore, when the probe plugs a jet, the pressure reading will improve over the initial reading as regurgitation caused by the jet will have been stopped, at least to some extent, by the probe acting as a transmitral rod or plug. By "improve" is meant that the ventricle pressure will show an increase and the atrial pressure a decrease over initial measurements. The surgeon will consequently have the exact position at which valve repair must occur. This is achieved without the need for imaging equipment, without affecting normal blood flow and without excessively invasive surgery.

The probe (450) can be operated to bend and hence move radially by a pull and/or push wire arrangement at the proximal end of the catheter. Such pull and/or push wire arrangements are well known in the art and will be apparent to those skilled in the art. Rotation of the probe is also achieved in a manner well known in the art, for example by rotating a connected element at the proximal end of the catheter.

Figure 20A:
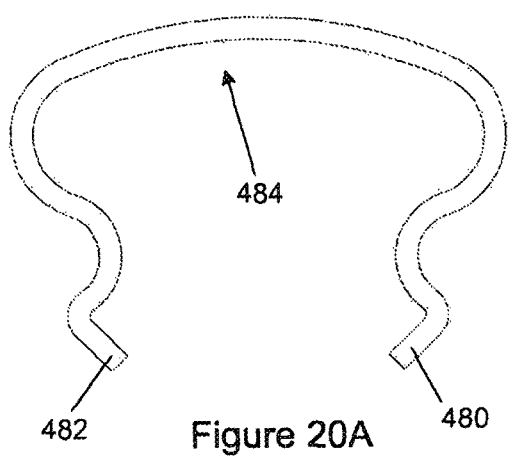
FIGS. 20A and 20B are anterior views of alternative embodiments of commissural arms of an orientation device.
Figure 20B:
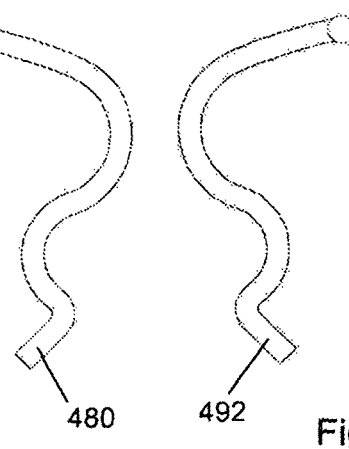

It will be appreciated that other embodiments exist. For example, an atrial anchor need not be provided integral with the commissural arms. As indicated in FIG. 20A the commissural arms (480, 482) could simply be joined together to form a continuous loop (484), or, as shown in FIG. 20B, the commissural arms (490, 492) could also be independent of each other. The commissural arms could also be formed from a single piece of shape memory material such as nitinol with a non-round cross-section. The arms may then be shape set in an open configuration and actuated using a pull and/or push wire arrangement or similar actuation method that will be apparent to those skilled in the art. The arms should, however, each extend generally within a plane in an operative condition. The arms should further extend from the catheter such that the plane in which each arm extends can be positioned perpendicularly relative to the plane of the mitral annulus. Typically this can be achieved with arms that extend co-planar with, or parallel to, the axis of the distal end of the catheter.

The atrial anchor could be provided on a separate catheter which could in turn be secured to the catheter carrying the commissural arms. The probe could also be carried on a separate catheter securable to either or both catheters and could itself include a pressure node or sensor on or near its tip.

It is important to be able to monitor pressure within the ventricle or atrium. While it is preferred to be able to monitor in both the ventricle and atrium simultaneously, this is not essential, as will be apparent from the above description. To assist the surgeon, the pressure measuring device could be supplied with an indicator which can be set at the initial reading so that a quick visual inspection indicates when initial pressure is reached. With analogue gauges using a needle to indicate a reading this is easily achieved by providing a separate movable index on the gauge. For digital gauges an alarm could be set for the initial pressure reading and triggered when reached. It is preferred to measure systolic pressure in the chambers but any suitable, repeatable pressure measurement could be used.

Also, any suitable atrial anchor could be used provided it is non-occlusive.

Figure 21:
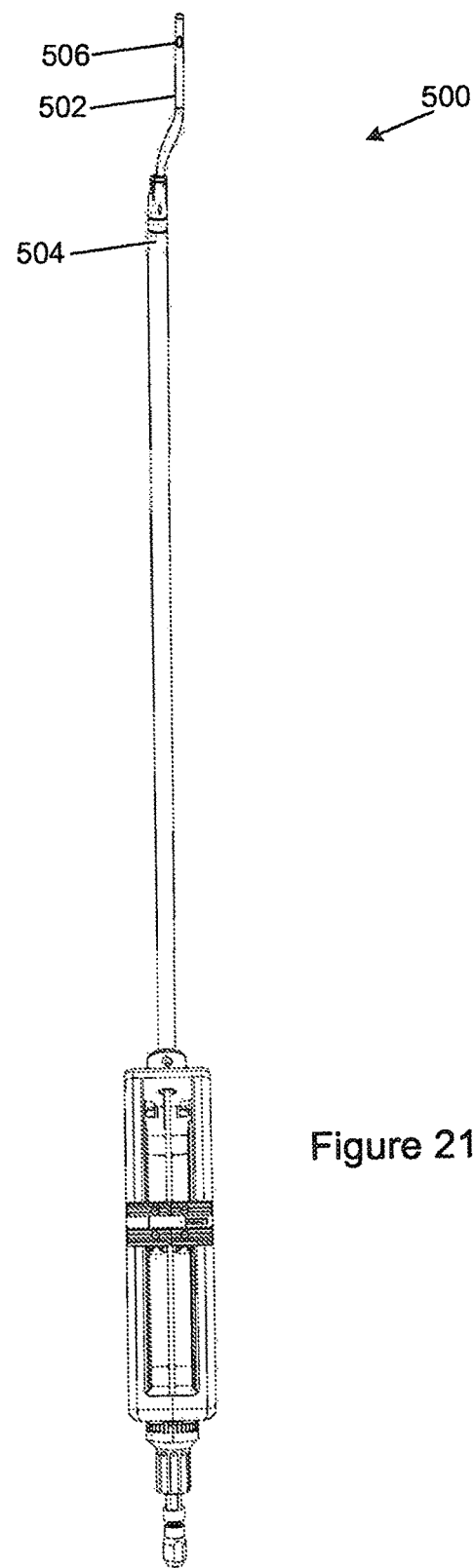
FIG. 21 is an anterior view of a manipulation device.

Referring to FIG. 21, a further embodiment provides a manipulation device (500) which includes a transmitral probe or rod (502) extending from a catheter (504) and having a pressure node (506) associated therewith and which can be secured to an anchor assembly located in a mitral valve. The anchor assembly will preferably include commissural arms and an atrial anchor substantially as described above and the probe (502) secured thereto, preferably through its associated catheter, to be movable relative thereto. The probe (502) may operatively extend into the zone of coaptation of a mitral valve to which the anchor assembly is secured to enable the valve to be manipulated and its geometry to be explored or determined, substantially as described above.

Conveniently, the manipulation device (500) could be secured to the anchor assembly by extending it through a passage in the catheter to which the anchor assembly is secured. Alternatively a slider could be provided which locates in a track on the anchor assembly catheter and which permits the manipulation device to be secured externally thereto. Many other methods of securing the manipulation device to an anchor assembly will be apparent to those skilled in the art.

Figure 22:
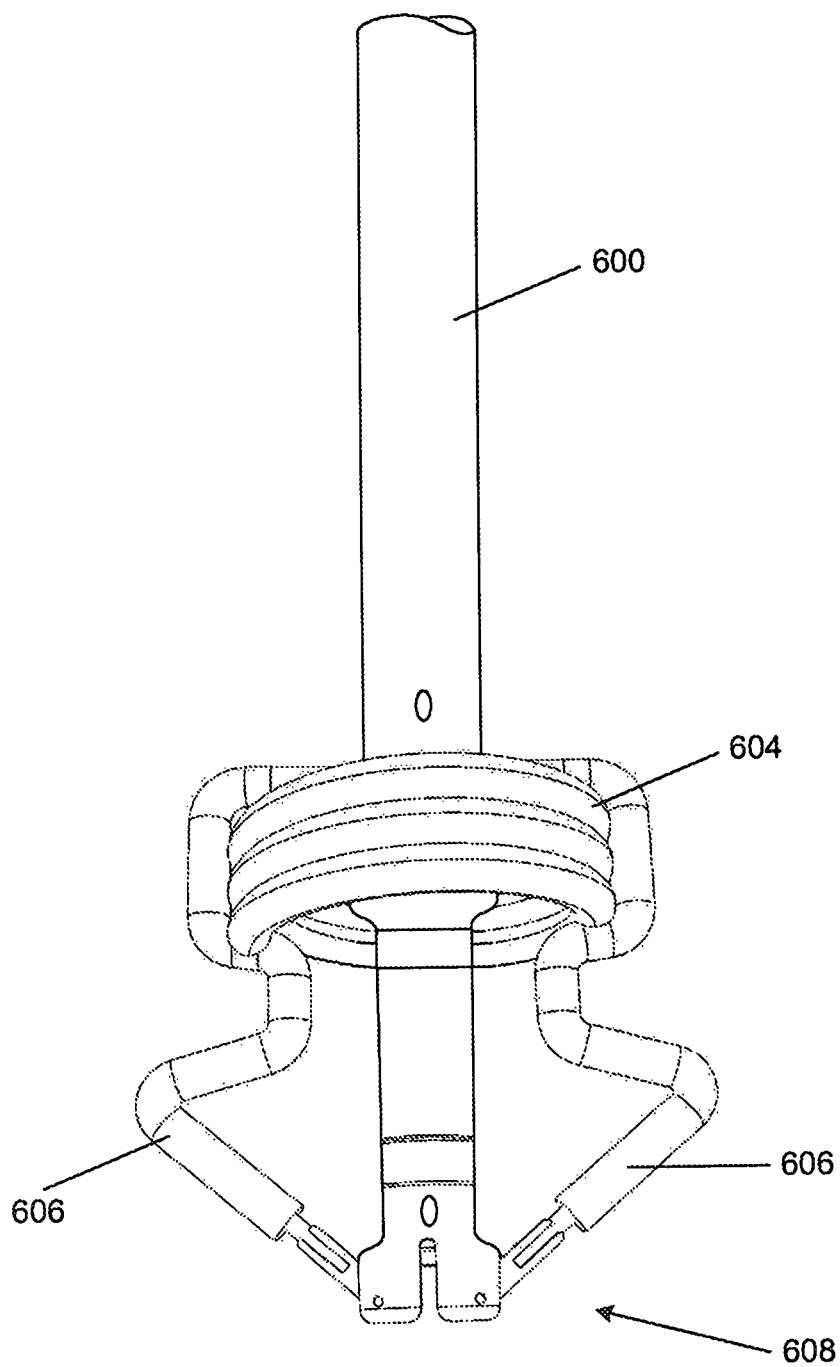
FIG. 22 is an anterior view of a further embodiment of an orientation device.

Adaptations required to enable the devices described above to be used in transfemoral or transaortic procedures, where required, will be readily apparent to those skilled in the art. Where the mitral valve is approached from the left atrium instead of the left ventricle, and the catheter inserted from the left atrium into the left ventricle through the mitral valve the orientation of operative elements, such as the commissural arms and the atrial anchor, on the catheter may be reversed to that of the embodiments described above. For example, as illustrated in FIG. 22, the catheter (600) can extend through the annulus of an inflatable helical atrial anchor (604) and between a pair of commissural arms (606) which are pivotally secured to the distal tip (608) of the catheter. The atrial anchor (604) and commissural arms (606) are substantially the same as those described with reference to FIG. 9 to 13. Their orientation on the catheter only is different, permitting the device to be used during and atrial entry in to the mitral valve.

As will be readily apparent to one skilled in the art, the principle of locating the device using pressure measurement and tactile feedback as described above remains the same whether approaching from the left atrium or the left ventricle.

The invention claimed is:

1. An orientation device for use in mitral valve repair surgery, the device including a catheter which is insertable percutaneously through the mitral valve into a chamber of a heart, the catheter having a distal end configured for entering the heart and a proximal end for manipulating the device, wherein the device includes at least one pressure sensor at or near the distal end of the catheter configured to sense pressures and/or pressure changes at or near the distal end of the catheter during navigation and/or orientation of the catheter within the heart to thereby at least partially indicate a location of the distal end of the catheter within the heart and/or whether the catheter has been properly oriented within the heart so as to not affect the functioning of the mitral valve, and for the device to include two commissural arms at or near the distal end of the catheter, the arms being deployable from a stowed condition, in which the catheter can be introduced percutaneously into the heart, to an operative condition in which the arms extend outwardly in generally opposite directions, each arm being shaped to be locatable within a mitral valve commissure to limit rotational movement of the catheter relative to the mitral valve without affecting the functioning of the valve.

2. An orientation device as claimed in claim 1, in which an indentation is provided in each arm and shaped to extend, in use, at least partially about a mitral valve commissure to limit movement thereof relative to the mitral valve in the axial direction of the catheter.

3. An orientation device as claimed in claim 1, in which the commissural arms include a pair of elongate flexible members that are individually operable and partially rotatable about the catheter.

4. An orientation device as claimed in claim 3, in which the elongate members are flexible wires which may be deployed to an operative arcuate condition by means of a pull and/or push wire arrangement.

5. An orientation device as claimed in claim 3, in which the elongate members are flexible wires each of which is manufactured from a shape memory alloy and is pre-formed to an arcuate shape and held in a deformed, relatively unbent shape during entry of the device into the heart, and returns to its pre-formed shape through manipulation of the device from its stowed condition to its operative condition.

6. An orientation device as claimed in claim 1, in which the commissural arms are tubular and capable of receiving a fluid therein and wherein at least part of each arm is inflatable.

7. An orientation device as claimed in claim 6, in which the arms are independently pivotable relative to the catheter.

8. An orientation device as claimed in claim 6, which includes a probe which extends from the catheter and which is movable relative to the commissural arms.

9. An orientation device as claimed in claim 1, in which an atrial anchor is associated with the distal end of the catheter and which can be deployed from an inoperative condition, in which it can be introduced percutaneously into the left atrium, to an operative condition, in which it forms an annular shape which is locatable in or over the mitral valve annulus and is too large to pass therethrough.

10. An orientation device as claimed in claim 9, in which the anchor has a helical shape in the operative condition.

11. An orientation device as claimed in claim 10, in which the atrial anchor is associated with the distal ends of the commissural arms and is located centrally between the arms.

12. An orientation device as claimed in claim 1, in which the at least one pressure sensor includes a first pressure sensor to be located at or near the distal end of the catheter and a second pressure sensor to be spaced apart therefrom.

13. A method of positioning an orientation device relative to a mitral valve, the orientation device including a catheter having a distal end configured for entering the heart and a proximal end for manipulating the device, the catheter including two commissural arms at or near the distal end, the method comprising the steps of:

extending the distal end of the catheter through the mitral valve from one of the left ventricle into the left atrium of a heart and the left atrium into the left ventricle of a heart, the catheter having at least one pressure sensor at or near its distal end, taking an initial pressure measurement in the left ventricle and an initial pressure measurement in the left atrium using the at least one pressure sensor, extending within the mitral valve the arms from the distal end of the catheter which arms project outwardly in generally opposite directions and are shaped to be locatable within a mitral valve commissure and have an indentation shaped to extend at least partially about a mitral valve commissure, measuring pressure in one or both of the left ventricle and left atrium and comparing the measurement to the corresponding initial pressure measurement, rotating the arms within the mitral valve if the measurement is not substantially similar to the corresponding initial pressure measurement, repeating the steps of measuring pressure in one or both of the left ventricle and left atrium, comparing the measurement to the corresponding initial pressure measurement and rotating the arms within the mitral valve if the measurement is not substantially similar to the corresponding initial pressure measurement until the measurement is substantially similar to the corresponding initial pressure measurement, and moving the arms axially within the valve until the indentation in each arm extends about a mitral valve commissure.

14. A method as claimed in claim 13, wherein an atrial anchor is associated with the distal ends of the commissural arms which can be deployed from an inoperative condition, in which it can be introduced percutaneously into the left atrium, to an operative condition, in which it forms an annular shape which is locatable in or over the mitral valve annulus, and for the method to include the step of, in response to the indentation in each arm extending about a mitral valve commissure, inflating the atrial anchor.

* * * * *